(12) United States Patent
Klimek et al.

(10) Patent No.: US 9,237,957 B2
(45) Date of Patent: *Jan. 19, 2016

(54) LOW PROFILE PLATE

(71) Applicant: Globus Medical, Inc., Audubon, PA (US)

(72) Inventors: Jennifer Klimek, King of Prussia, PA (US); Stephan Lawson, Darby, PA (US); Samuel Petersheim, Elverson, PA (US); Jason Cianfrani, East Norriton, PA (US); Kyle Rosen, Gilbertsville, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/190,948

(22) Filed: Feb. 26, 2014

(65) Prior Publication Data

US 2014/0180422 A1 Jun. 26, 2014

Related U.S. Application Data

(63) Continuation-in-part of application No. 13/785,434, filed on Mar. 5, 2013, now Pat. No. 9,149,365, and a continuation-in-part of application No. 14/085,318, filed on Nov. 20, 2013, which is a continuation-in-part of application No. 13/785,856, filed on Mar. 5, 2013, which is a continuation-in-part of application No. 13/559,917, filed on Jul. 27, 2012, now Pat. No. 8,961,606, which is a continuation-in-part of application No. 13/267,119, filed on Oct. 6, 2011.

(60) Provisional application No. 61/535,726, filed on Sep. 16, 2011.

(51) Int. Cl.
*A61F 2/44* (2006.01)
*A61F 2/30* (2006.01)
(Continued)

(52) U.S. Cl.
CPC ............ *A61F 2/447* (2013.01); *A61B 17/8042* (2013.01); *A61F 2/30744* (2013.01); *A61F 2/4611* (2013.01); *A61F 2002/305* (2013.01); *A61F 2002/308* (2013.01); *A61F 2002/30131* (2013.01); *A61F 2002/30492* (2013.01); *A61F 2002/30504* (2013.01); *A61F 2002/30787* (2013.01); *A61F 2002/30808* (2013.01); *A61F 2002/30828* (2013.01); *A61F 2002/30836* (2013.01); *A61F 2002/30848* (2013.01); *A61F 2002/30884* (2013.01); *A61F 2002/30904* (2013.01); *A61F 2002/4475* (2013.01); *A61F 2310/00359* (2013.01)

(58) Field of Classification Search
CPC ......... A61F 2/44; A61F 2/4455; A61F 2/447; A61F 2002/30131; A61F 2002/30504; A61F 2002/4475
USPC .............................. 623/17.11–17.16
See application file for complete search history.

(56) References Cited

U.S. PATENT DOCUMENTS

| | | |
|---|---|---|
| 1,673,630 A | 6/1928 | Madge |
| 2,363,405 A | 11/1944 | Eichelberger |

(Continued)

*Primary Examiner* — Christian Sevilla
*Assistant Examiner* — Eric S Gibson

(57) ABSTRACT

The present application generally relates to orthopedic systems, and in particular, to systems including independent plates and spacers. A plating system can include a spacer and a plate that is independent from the spacer. A number of locking mechanisms can be provided to secure the plate to the spacer. In some cases, the spacer includes a pair of notches that extend on an outer surface of the spacer. The plate can include a pair of lateral extensions that can engage the notches to secure the plate to the spacer. In other cases, the spacer includes an opening including a pair of inlets. The plate can include an enclosed posterior extension that can be received in the pair of inlets to secure the plate to the spacer.

16 Claims, 14 Drawing Sheets

(51) Int. Cl.
  *A61B 17/80* (2006.01)
  *A61F 2/46* (2006.01)

(56) References Cited

U.S. PATENT DOCUMENTS

| | | |
|---|---|---|
| 2,596,957 A | 5/1952 | Olson |
| 4,599,086 A | 7/1986 | Doty |
| 4,743,256 A | 5/1988 | Brantigan |
| 4,955,908 A | 9/1990 | Frey |
| 5,002,576 A | 3/1991 | Fuhrmann |
| 5,163,949 A | 11/1992 | Bonutti |
| 5,163,960 A | 11/1992 | Bonutti |
| 5,197,971 A | 3/1993 | Bonutti |
| 5,269,785 A | 12/1993 | Bonutti |
| 5,295,994 A | 3/1994 | Bonutti |
| 5,329,846 A | 7/1994 | Bonutti |
| 5,331,975 A | 7/1994 | Bonutti |
| 5,345,927 A | 9/1994 | Bonutti |
| 5,364,399 A | 11/1994 | Lowery |
| 5,397,364 A | 3/1995 | Kozak |
| 5,403,317 A | 4/1995 | Bonutti |
| 5,403,348 A | 4/1995 | Bonutti |
| 5,441,538 A | 8/1995 | Bonutti |
| 5,454,365 A | 10/1995 | Bonutti |
| 5,464,426 A | 11/1995 | Bonutti |
| 5,496,348 A | 3/1996 | Bonutti |
| 5,514,153 A | 5/1996 | Bonutti |
| 5,514,180 A | 5/1996 | Heggeness |
| 5,522,846 A | 6/1996 | Bonutti |
| 5,527,343 A | 6/1996 | Bonutti |
| 5,534,012 A | 7/1996 | Bonutti |
| 5,545,222 A | 8/1996 | Bonutti |
| 5,549,630 A | 8/1996 | Bonutti |
| 5,549,631 A | 8/1996 | Bonutti |
| 5,569,305 A | 10/1996 | Bonutti |
| 5,577,517 A | 11/1996 | Bonutti |
| 5,584,862 A | 12/1996 | Bonutti |
| 5,593,425 A | 1/1997 | Bonutti |
| 5,609,635 A | 3/1997 | Michelson |
| 5,624,462 A | 4/1997 | Bonutti |
| 5,662,710 A | 9/1997 | Bonutti |
| 5,667,520 A | 9/1997 | Bonutti |
| 5,685,826 A | 11/1997 | Bonutti |
| 5,694,951 A | 12/1997 | Bonutti |
| 5,707,390 A | 1/1998 | Bonutti |
| 5,716,325 A | 2/1998 | Bonutti |
| 5,728,159 A | 3/1998 | Stroever |
| 5,733,306 A | 3/1998 | Bonutti |
| 5,735,875 A | 4/1998 | Bonutti |
| 5,741,253 A | 4/1998 | Michelson |
| 5,814,084 A | 9/1998 | Grivas |
| 5,827,318 A | 10/1998 | Bonutti |
| 5,845,645 A | 12/1998 | Bonutti |
| 5,860,997 A | 1/1999 | Bonutti |
| 5,861,041 A | 1/1999 | Tienboon |
| 5,888,196 A | 3/1999 | Bonutti |
| 5,888,219 A | 3/1999 | Bonutti |
| 5,888,223 A | 3/1999 | Bray, Jr. |
| 5,888,227 A | 3/1999 | Cottle |
| 5,899,939 A | 5/1999 | Boyce |
| 5,928,267 A | 7/1999 | Bonutti |
| 5,935,131 A | 8/1999 | Bonutti |
| 5,941,900 A | 8/1999 | Bonutti |
| 5,954,739 A | 9/1999 | Bonutti |
| 5,972,368 A | 10/1999 | Mckay |
| 5,989,289 A | 11/1999 | Coates |
| 6,010,525 A | 1/2000 | Bonutti |
| 6,017,305 A | 1/2000 | Bonutti |
| 6,025,538 A | 2/2000 | Yaccarino, III |
| 6,033,438 A | 3/2000 | Bianchi |
| 6,042,596 A | 3/2000 | Bonutti |
| 6,045,579 A | 4/2000 | Hochshuler |
| 6,059,817 A | 5/2000 | Bonutti |
| 6,077,292 A | 6/2000 | Bonutti |
| 6,086,593 A | 7/2000 | Bonutti |
| 6,096,081 A | 8/2000 | Grivas |
| 6,099,531 A | 8/2000 | Bonutti |
| 6,102,928 A | 8/2000 | Bonutti |
| 6,132,472 A | 10/2000 | Bonutti |
| RE36,974 E | 11/2000 | Bonutti |
| 6,143,033 A | 11/2000 | Paul |
| 6,146,421 A | 11/2000 | Gordon |
| 6,159,234 A | 12/2000 | Bonutti |
| 6,171,236 B1 | 1/2001 | Bonutti |
| 6,171,299 B1 | 1/2001 | Bonutti |
| 6,174,311 B1 | 1/2001 | Branch |
| 6,174,313 B1 | 1/2001 | Bonutti |
| 6,187,023 B1 | 2/2001 | Bonutti |
| 6,203,565 B1 | 3/2001 | Bonutti |
| 6,206,923 B1 | 3/2001 | Boyd |
| 6,217,617 B1 | 4/2001 | Bonutti |
| 6,231,592 B1 | 5/2001 | Bonutti |
| 6,231,610 B1 | 5/2001 | Geisler |
| 6,235,059 B1 | 5/2001 | Benezech |
| 6,245,108 B1 | 6/2001 | Biscup |
| 6,258,125 B1 * | 7/2001 | Paul et al. ............... 623/17.11 |
| 6,261,586 B1 | 7/2001 | Mckay |
| 6,270,528 B1 | 8/2001 | Mckay |
| 6,277,136 B1 | 8/2001 | Bonutti |
| 6,287,325 B1 | 9/2001 | Bonutti |
| 6,294,187 B1 | 9/2001 | Boyce |
| 6,342,074 B1 | 1/2002 | Simpson |
| 6,350,283 B1 | 2/2002 | Michelson |
| 6,358,266 B1 | 3/2002 | Bonutti |
| 6,361,565 B1 | 3/2002 | Bonutti |
| 6,364,880 B1 | 4/2002 | Michelson |
| 6,368,343 B1 | 4/2002 | Bonutti |
| 6,371,988 B1 | 4/2002 | Pafford |
| 6,379,385 B1 | 4/2002 | Kalas |
| 6,398,811 B1 | 6/2002 | Mckay |
| 6,409,765 B1 | 6/2002 | Bianchi |
| 6,432,106 B1 | 8/2002 | Fraser |
| 6,432,436 B1 | 8/2002 | Gertzman |
| 6,447,516 B1 | 9/2002 | Bonutti |
| 6,451,042 B1 | 9/2002 | Bonutti |
| 6,458,158 B1 | 10/2002 | Anderson |
| 6,464,713 B2 | 10/2002 | Bonutti |
| 6,468,289 B1 | 10/2002 | Bonutti |
| 6,468,293 B2 | 10/2002 | Bonutti |
| 6,468,311 B2 | 10/2002 | Boyd |
| 6,471,724 B2 | 10/2002 | Zdeblick |
| 6,475,230 B1 | 11/2002 | Bonutti |
| 6,482,233 B1 | 11/2002 | Aebi |
| 6,500,195 B2 | 12/2002 | Bonutti |
| 6,503,267 B2 | 1/2003 | Bonutti |
| 6,503,277 B2 | 1/2003 | Bonutti |
| 6,511,509 B1 | 1/2003 | Ford |
| 6,520,993 B2 | 2/2003 | James |
| 6,543,455 B2 | 4/2003 | Bonutti |
| 6,548,080 B1 | 4/2003 | Gertzman |
| 6,554,863 B2 | 4/2003 | Paul |
| 6,558,387 B2 | 5/2003 | Errico |
| 6,558,423 B1 | 5/2003 | Michelson |
| 6,562,073 B2 | 5/2003 | Foley |
| 6,569,187 B1 | 5/2003 | Bonutti |
| 6,575,982 B1 | 6/2003 | Bonutti |
| 6,579,318 B2 | 6/2003 | Varga |
| 6,585,750 B2 | 7/2003 | Bonutti |
| 6,592,531 B2 | 7/2003 | Bonutti |
| 6,592,609 B1 | 7/2003 | Bonutti |
| 6,607,534 B2 | 8/2003 | Bonutti |
| 6,610,065 B1 | 8/2003 | Branch |
| 6,620,181 B1 | 9/2003 | Bonutti |
| 6,629,998 B1 | 10/2003 | Lin |
| 6,630,000 B1 | 10/2003 | Bonutti |
| 6,632,247 B2 | 10/2003 | Boyer, II |
| 6,635,073 B2 | 10/2003 | Bonutti |
| 6,638,309 B2 | 10/2003 | Bonutti |
| 6,638,310 B2 | 10/2003 | Lin |
| 6,652,532 B2 | 11/2003 | Bonutti |
| 6,652,593 B2 | 11/2003 | Boyer, II |
| 6,660,038 B2 | 12/2003 | Boyer, II |
| 6,666,890 B2 | 12/2003 | Michelson |
| 6,676,703 B2 | 1/2004 | Biscup |

(56) References Cited

U.S. PATENT DOCUMENTS

| | | | | |
|---|---|---|---|---|
| 6,682,563 | B2 | 1/2004 | Scharf | |
| 6,695,882 | B2 | 2/2004 | Bianchi | |
| 6,702,821 | B2 | 3/2004 | Bonutti | |
| 6,702,856 | B2 | 3/2004 | Bonutti | |
| 6,706,067 | B2 | 3/2004 | Shimp | |
| 6,706,087 | B1 | 3/2004 | Shimp et al. | |
| 6,709,458 | B2 | 3/2004 | Michelson | |
| 6,719,794 | B2 | 4/2004 | Gerber | |
| 6,719,803 | B2 | 4/2004 | Bonutti | |
| 6,730,127 | B2 | 5/2004 | Michelson | |
| 6,736,853 | B2 | 5/2004 | Bonutti | |
| 6,761,738 | B1 | 7/2004 | Boyd | |
| 6,761,739 | B2 | 7/2004 | Shepard | |
| 6,764,491 | B2 | 7/2004 | Frey | |
| 6,767,369 | B2 | 7/2004 | Boyer, II | |
| 6,770,078 | B2 | 8/2004 | Bonutti | |
| 6,776,800 | B2 | 8/2004 | Boyer, II | |
| 6,776,938 | B2 | 8/2004 | Bonutti | |
| 6,793,658 | B2 | 9/2004 | LeHuec | |
| RE38,614 | E | 10/2004 | Paul | |
| 6,805,714 | B2 | 10/2004 | Sutcliffe | |
| 6,808,585 | B2 | 10/2004 | Boyce | |
| 6,830,570 | B1 | 12/2004 | Frey | |
| 6,835,198 | B2 | 12/2004 | Bonutti | |
| 6,835,206 | B2 | 12/2004 | Jackson | |
| 6,849,093 | B2 | 2/2005 | Michelson | |
| 6,852,126 | B2 | 2/2005 | Ahlgren | |
| 6,855,167 | B2 | 2/2005 | Shimp | |
| 6,855,169 | B2 | 2/2005 | Boyer, II | |
| 6,860,885 | B2 | 3/2005 | Bonutti | |
| 6,860,904 | B2 | 3/2005 | Bonutti | |
| 6,887,272 | B2 | 5/2005 | Shinomiya | |
| 6,902,578 | B1 * | 6/2005 | Anderson | A61F 2/28 623/16.11 |
| 6,905,517 | B2 | 6/2005 | Bonutti | |
| 6,908,466 | B1 | 6/2005 | Bonutti | |
| 6,929,662 | B1 | 8/2005 | Messerli | |
| 6,932,835 | B2 | 8/2005 | Bonutti | |
| 6,974,480 | B2 | 12/2005 | Messerli | |
| 6,986,788 | B2 * | 1/2006 | Paul et al. | 623/17.11 |
| 6,989,029 | B2 | 1/2006 | Bonutti | |
| 6,990,982 | B1 | 1/2006 | Bonutti | |
| 7,014,659 | B2 | 3/2006 | Boyer, II | |
| 7,018,412 | B2 | 3/2006 | Ferreira | |
| 7,018,413 | B2 | 3/2006 | Krüger | |
| 7,022,137 | B2 | 4/2006 | Michelson | |
| 7,044,968 | B1 | 5/2006 | Yaccarino, III | |
| 7,044,972 | B2 | 5/2006 | Mathys | |
| 7,048,755 | B2 | 5/2006 | Bonutti | |
| 7,048,762 | B1 | 5/2006 | Sander | |
| 7,048,765 | B1 | 5/2006 | Grooms | |
| 7,060,073 | B2 | 6/2006 | Frey | |
| 7,060,096 | B1 | 6/2006 | Schopf | |
| 7,070,557 | B2 | 7/2006 | Bonutti | |
| 7,087,073 | B2 | 8/2006 | Bonutti | |
| 7,087,082 | B2 | 8/2006 | Paul | |
| 7,087,087 | B2 | 8/2006 | Boyer, II | |
| 7,094,251 | B2 | 8/2006 | Bonutti | |
| 7,104,996 | B2 | 9/2006 | Bonutti | |
| 7,112,222 | B2 | 9/2006 | Fraser | |
| 7,114,500 | B2 | 10/2006 | Bonutti | |
| 7,115,146 | B2 | 10/2006 | Boyer, II | |
| 7,128,753 | B1 | 10/2006 | Bonutti | |
| 7,134,437 | B2 | 11/2006 | Bonutti | |
| 7,147,652 | B2 | 12/2006 | Bonutti | |
| 7,163,561 | B2 | 1/2007 | Michelson | |
| 7,172,627 | B2 | 2/2007 | Fiere | |
| 7,192,447 | B2 | 3/2007 | Rhoda | |
| 7,208,013 | B1 | 4/2007 | Bonutti | |
| 7,217,273 | B2 | 5/2007 | Bonutti | |
| 7,217,290 | B2 | 5/2007 | Bonutti | |
| 7,223,292 | B2 | 5/2007 | Messerli | |
| 7,226,482 | B2 * | 6/2007 | Messerli et al. | 623/17.11 |
| 7,226,483 | B2 | 6/2007 | Gerber | |
| 7,229,477 | B2 | 6/2007 | Biscup | |
| 7,232,464 | B2 | 6/2007 | Mathieu | |
| 7,238,203 | B2 | 7/2007 | Bagga | |
| 7,300,465 | B2 | 11/2007 | Paul | |
| 7,309,357 | B2 | 12/2007 | Kim | |
| 7,309,359 | B2 | 12/2007 | Trieu | |
| 7,311,719 | B2 | 12/2007 | Bonutti | |
| 7,323,011 | B2 * | 1/2008 | Shepard et al. | 623/17.11 |
| 7,329,263 | B2 | 2/2008 | Bonutti | |
| 7,347,873 | B2 | 3/2008 | Paul | |
| 7,429,266 | B2 | 9/2008 | Bonutti | |
| 7,435,262 | B2 | 10/2008 | Michelson | |
| 7,462,200 | B2 | 12/2008 | Bonutti | |
| 7,473,277 | B2 | 1/2009 | Boyer, II | |
| 7,479,160 | B2 | 1/2009 | Branch | |
| 7,481,812 | B2 | 1/2009 | Frey | |
| 7,481,831 | B2 | 1/2009 | Bonutti | |
| 7,491,237 | B2 * | 2/2009 | Randall et al. | 623/17.11 |
| 7,510,557 | B1 | 3/2009 | Bonutti | |
| 7,594,931 | B2 | 9/2009 | Louis | |
| 7,601,173 | B2 | 10/2009 | Messerli | |
| 7,615,054 | B1 | 11/2009 | Bonutti | |
| 7,618,456 | B2 | 11/2009 | Mathieu | |
| 7,618,460 | B2 | 11/2009 | Boyd | |
| 7,635,390 | B1 | 12/2009 | Bonutti | |
| 7,637,953 | B2 | 12/2009 | Branch | |
| 7,662,184 | B2 | 2/2010 | Edwards | |
| 7,662,185 | B2 | 2/2010 | Alfaro | |
| 7,708,740 | B1 | 5/2010 | Bonutti | |
| 7,708,741 | B1 | 5/2010 | Bonutti | |
| 7,726,002 | B2 | 6/2010 | Shimp | |
| 7,727,283 | B2 | 6/2010 | Bonutti | |
| 7,749,229 | B1 | 7/2010 | Bonutti | |
| 7,753,963 | B2 | 7/2010 | Boyer, II | |
| 7,780,670 | B2 | 8/2010 | Bonutti | |
| 7,794,502 | B2 | 9/2010 | Michelson | |
| 7,806,896 | B1 | 10/2010 | Bonutti | |
| 7,806,897 | B1 | 10/2010 | Bonutti | |
| 7,815,682 | B1 | 10/2010 | Peterson | |
| 7,828,852 | B2 | 11/2010 | Bonutti | |
| 7,833,271 | B2 | 11/2010 | Mitchell | |
| 7,837,736 | B2 | 11/2010 | Bonutti | |
| 7,846,207 | B2 | 12/2010 | Lechmann | |
| 7,850,731 | B2 | 12/2010 | Brittan | |
| 7,854,750 | B2 | 12/2010 | Bonutti | |
| 7,862,616 | B2 | 1/2011 | Lechmann | |
| 7,875,076 | B2 | 1/2011 | Mathieu | |
| 7,875,080 | B2 * | 1/2011 | Puno et al. | 623/17.16 |
| 7,879,072 | B2 | 2/2011 | Bonutti | |
| 7,879,103 | B2 | 2/2011 | Gertzman | |
| 7,892,236 | B1 | 2/2011 | Bonutti | |
| 7,892,261 | B2 | 2/2011 | Bonutti | |
| 7,896,880 | B2 | 3/2011 | Bonutti | |
| 7,918,888 | B2 | 4/2011 | Hamada | |
| 7,931,690 | B1 | 4/2011 | Bonutti | |
| 7,931,692 | B2 | 4/2011 | Sybert | |
| 7,938,857 | B2 | 5/2011 | Garcia-bengochea | |
| 7,959,635 | B1 | 6/2011 | Bonutti | |
| 7,967,867 | B2 | 6/2011 | Barreiro | |
| 7,972,381 | B2 | 7/2011 | Michelson | |
| 8,002,833 | B2 | 8/2011 | Fabris Monterumici | |
| 8,100,976 | B2 * | 1/2012 | Bray et al. | 623/17.16 |
| 8,105,383 | B2 | 1/2012 | Michelson | |
| 8,114,162 | B1 | 2/2012 | Bradley | |
| 8,128,669 | B2 | 3/2012 | Bonutti | |
| 8,133,229 | B1 | 3/2012 | Bonutti | |
| 8,162,977 | B2 | 4/2012 | Bonutti | |
| 8,273,127 | B2 | 9/2012 | Jones | |
| 8,323,343 | B2 | 12/2012 | Michelson | |
| 8,328,872 | B2 | 12/2012 | Duffield | |
| 8,366,776 | B2 | 2/2013 | Heinz | |
| 8,425,522 | B2 | 4/2013 | Bonutti | |
| 8,435,300 | B2 | 5/2013 | Messerli | |
| 8,486,066 | B2 | 7/2013 | Bonutti | |
| 8,623,030 | B2 | 1/2014 | Bonutti | |
| 8,632,552 | B2 | 1/2014 | Bonutti | |
| 8,641,726 | B2 | 2/2014 | Bonutti | |
| 8,690,928 | B1 * | 4/2014 | Walkenhorst et al. | 606/287 |
| 8,690,944 | B2 | 4/2014 | Bonutti | |
| 8,709,085 | B2 | 4/2014 | Lechmann | |

(56) References Cited

U.S. PATENT DOCUMENTS

| | | |
|---|---|---|
| 8,728,165 B2 * | 5/2014 | Parry et al. .................. 623/17.16 |
| 8,739,797 B2 | 6/2014 | Bonutti |
| 8,747,439 B2 | 6/2014 | Bonutti |
| 8,784,495 B2 | 7/2014 | Bonutti |
| 8,795,363 B2 | 8/2014 | Bonutti |
| 8,814,902 B2 | 8/2014 | Bonutti |
| 8,834,490 B2 | 9/2014 | Bonutti |
| 8,840,629 B2 | 9/2014 | Bonutti |
| 8,845,699 B2 | 9/2014 | Bonutti |
| 8,858,557 B2 | 10/2014 | Bonutti |
| 8,900,309 B2 * | 12/2014 | James et al. ................ 623/17.16 |
| 8,956,417 B2 | 2/2015 | Bonutti |
| 9,044,322 B2 | 6/2015 | Bonutti |
| 9,044,341 B2 | 6/2015 | Bonutti |
| 9,050,152 B2 | 6/2015 | Bonutti |
| 2001/0010021 A1 | 7/2001 | Boyd |
| 2001/0023371 A1 | 9/2001 | Bonutti |
| 2002/0029055 A1 | 3/2002 | Bonutti |
| 2002/0040246 A1 | 4/2002 | Bonutti |
| 2002/0095160 A1 | 7/2002 | Bonutti |
| 2002/0106393 A1 * | 8/2002 | Bianchi et al. ................. 424/423 |
| 2002/0138143 A1 | 9/2002 | Grooms |
| 2003/0009147 A1 | 1/2003 | Bonutti |
| 2003/0023260 A1 | 1/2003 | Bonutti |
| 2004/0010287 A1 | 1/2004 | Bonutti |
| 2004/0097794 A1 | 5/2004 | Bonutti |
| 2004/0098016 A1 | 5/2004 | Bonutti |
| 2004/0122518 A1 * | 6/2004 | Rhoda ........................ 623/17.11 |
| 2004/0138689 A1 | 7/2004 | Bonutti |
| 2004/0138690 A1 | 7/2004 | Bonutti |
| 2004/0143285 A1 | 7/2004 | Bonutti |
| 2004/0172033 A1 | 9/2004 | Bonutti |
| 2004/0172133 A1 | 9/2004 | Gerber |
| 2004/0193181 A1 | 9/2004 | Bonutti |
| 2004/0210219 A1 * | 10/2004 | Bray .............................. 606/69 |
| 2004/0230223 A1 | 11/2004 | Bonutti |
| 2005/0216059 A1 | 9/2005 | Bonutti |
| 2005/0267534 A1 | 12/2005 | Bonutti |
| 2006/0030851 A1 * | 2/2006 | Bray et al. ....................... 606/69 |
| 2006/0085071 A1 * | 4/2006 | Lechmann et al. .......... 623/17.11 |
| 2006/0142828 A1 | 6/2006 | Schorr |
| 2006/0167495 A1 | 7/2006 | Bonutti |
| 2006/0235470 A1 | 10/2006 | Bonutti |
| 2006/0241760 A1 * | 10/2006 | Randall et al. .............. 623/17.11 |
| 2006/0265009 A1 | 11/2006 | Bonutti |
| 2007/0106388 A1 * | 5/2007 | Michelson .................. 623/17.16 |
| 2007/0208378 A1 | 9/2007 | Bonutti |
| 2007/0250167 A1 | 10/2007 | Bray |
| 2007/0255414 A1 | 11/2007 | Melkent |
| 2008/0039873 A1 | 2/2008 | Bonutti |
| 2008/0046090 A1 | 2/2008 | Paul |
| 2008/0047567 A1 | 2/2008 | Bonutti |
| 2008/0058822 A1 | 3/2008 | Bonutti |
| 2008/0065140 A1 | 3/2008 | Bonutti |
| 2008/0103519 A1 | 5/2008 | Bonutti |
| 2008/0108916 A1 | 5/2008 | Bonutti |
| 2008/0114399 A1 | 5/2008 | Bonutti |
| 2008/0125865 A1 | 5/2008 | Abdelgany |
| 2008/0140011 A1 | 6/2008 | Bonutti |
| 2008/0140117 A1 | 6/2008 | Bonutti |
| 2008/0154379 A1 | 6/2008 | Steiner |
| 2008/0177307 A1 * | 7/2008 | Moskowitz et al. .......... 606/246 |
| 2008/0188940 A1 | 8/2008 | Cohen |
| 2008/0249569 A1 * | 10/2008 | Waugh et al. ................ 606/249 |
| 2008/0249625 A1 * | 10/2008 | Waugh et al. ................ 623/17.16 |
| 2008/0269806 A1 * | 10/2008 | Zhang et al. .................. 606/286 |
| 2008/0281425 A1 * | 11/2008 | Thalgott et al. ............. 623/17.16 |
| 2008/0306596 A1 * | 12/2008 | Jones et al. .................. 623/17.16 |
| 2009/0088849 A1 * | 4/2009 | Armstrong et al. .......... 623/17.16 |
| 2009/0099661 A1 | 4/2009 | Bhattacharya |
| 2009/0101582 A1 | 4/2009 | Liu |
| 2009/0105831 A1 * | 4/2009 | Jones et al. .................. 623/17.16 |
| 2009/0210062 A1 * | 8/2009 | Thalgott et al. ............. 623/17.16 |
| 2009/0234455 A1 * | 9/2009 | Moskowitz et al. ......... 623/17.11 |
| 2010/0057206 A1 * | 3/2010 | Duffield et al. ............. 623/17.16 |
| 2010/0145459 A1 | 6/2010 | McDonough |
| 2010/0145460 A1 * | 6/2010 | McDonough et al. ...... 623/17.16 |
| 2010/0305704 A1 * | 12/2010 | Messerli et al. ............. 623/17.16 |
| 2010/0312345 A1 * | 12/2010 | Duffield et al. ............. 623/17.16 |
| 2010/0312346 A1 * | 12/2010 | Kueenzi et al. ............. 623/17.16 |
| 2011/0087327 A1 | 4/2011 | Lechmann |
| 2011/0160864 A1 | 6/2011 | Messerli |
| 2011/0160866 A1 * | 6/2011 | Laurence et al. ............ 623/17.16 |
| 2011/0230971 A1 * | 9/2011 | Donner et al. ............. 623/17.16 |
| 2011/0251689 A1 * | 10/2011 | Seifert et al. ................ 623/17.16 |
| 2012/0010623 A1 | 1/2012 | Bonutti |
| 2012/0078373 A1 * | 3/2012 | Gamache et al. ............ 623/17.16 |
| 2012/0130495 A1 | 5/2012 | Duffield |
| 2012/0130496 A1 | 5/2012 | Duffield |
| 2012/0179259 A1 * | 7/2012 | McDonough et al. ...... 623/17.16 |
| 2012/0197401 A1 * | 8/2012 | Duncan et al. .............. 623/17.16 |
| 2012/0209385 A1 * | 8/2012 | Aferzon ...................... 623/17.16 |
| 2012/0215226 A1 | 8/2012 | Bonutti |
| 2012/0215233 A1 | 8/2012 | Bonutti |
| 2012/0215313 A1 * | 8/2012 | Saidha et al. ................ 623/17.16 |
| 2012/0221017 A1 | 8/2012 | Bonutti |
| 2012/0277867 A1 * | 11/2012 | Kana et al. .................. 623/17.16 |
| 2012/0277870 A1 * | 11/2012 | Wolters et al. .............. 623/17.16 |
| 2012/0277872 A1 * | 11/2012 | Kana et al. .................. 623/17.16 |
| 2012/0277873 A1 * | 11/2012 | Kana et al. .................. 623/17.16 |
| 2012/0323330 A1 | 12/2012 | Kueenzi |
| 2013/0018470 A1 * | 1/2013 | Moskowitz et al. ......... 623/17.16 |
| 2013/0073046 A1 * | 3/2013 | Zaveloff et al. ............. 623/17.16 |
| 2013/0073047 A1 * | 3/2013 | Laskowitz ............ A61F 2/4455 623/17.16 |
| 2013/0166032 A1 * | 6/2013 | McDonough et al. ...... 623/17.16 |
| 2013/0211523 A1 * | 8/2013 | Southard et al. ........... 623/16.11 |
| 2013/0218276 A1 * | 8/2013 | Fiechter et al. ............. 623/17.16 |
| 2013/0226185 A1 | 8/2013 | Bonutti |
| 2013/0237989 A1 | 9/2013 | Bonutti |
| 2013/0289729 A1 | 10/2013 | Bonutti |
| 2013/0297029 A1 * | 11/2013 | Kana et al. .................. 623/17.16 |
| 2014/0012380 A1 * | 1/2014 | Laurence et al. ............ 623/17.16 |
| 2014/0012384 A1 * | 1/2014 | Kana et al. .................. 623/17.16 |
| 2014/0018854 A1 | 1/2014 | Bonutti |
| 2014/0025110 A1 | 1/2014 | Bonutti |
| 2014/0025111 A1 | 1/2014 | Bonutti |
| 2014/0025112 A1 | 1/2014 | Bonutti |
| 2014/0039623 A1 * | 2/2014 | Lott et al. .................... 623/17.16 |
| 2014/0052258 A1 * | 2/2014 | Ball et al. .................... 623/17.16 |
| 2014/0058520 A1 * | 2/2014 | Crozet ........................ 623/17.16 |
| 2014/0180422 A1 * | 6/2014 | Klimek et al. .............. 623/17.16 |
| 2014/0214166 A1 * | 7/2014 | Theofilos ............ A61F 2/4455 623/17.16 |
| 2014/0214167 A1 * | 7/2014 | Theofilos et al. ........... 623/17.16 |
| 2014/0228963 A1 | 8/2014 | Bonutti |
| 2014/0243985 A1 * | 8/2014 | Lechmann et al. .......... 623/17.16 |
| 2014/0257380 A1 | 9/2014 | Bonutti |
| 2014/0257487 A1 * | 9/2014 | Lawson et al. .............. 623/17.16 |
| 2014/0277456 A1 * | 9/2014 | Kirschman .................. 623/17.11 |
| 2014/0277488 A1 * | 9/2014 | Davenport et al. .......... 623/17.16 |
| 2014/0277489 A1 * | 9/2014 | Davenport et al. .......... 623/17.16 |
| 2014/0277497 A1 * | 9/2014 | Bennett et al. .............. 623/17.16 |
| 2014/0309585 A1 | 10/2014 | Bonutti |
| 2014/0330383 A1 * | 11/2014 | Wimberley et al. ......... 623/17.16 |
| 2014/0330385 A1 * | 11/2014 | Carlson et al. .............. 623/17.16 |
| 2014/0336770 A1 * | 11/2014 | Petersheim et al. ......... 623/17.16 |
| 2014/0343573 A1 | 11/2014 | Bonutti |
| 2014/0371859 A1 * | 12/2014 | Petersheim et al. ......... 623/17.16 |

* cited by examiner

LOW PROFILE PLATE

CROSS-REFERENCE TO RELATED APPLICATIONS

The present application is a continuation-in-part application of U.S. Ser. No. 13/785,434, filed Mar. 5, 2013 and of U.S. Ser. No. 14/085,318, filed Nov. 20, 2013, which is a continuation-in-part application of U.S. patent application Ser. No. 13/785,856, filed Mar. 5, 2013, which is a continuation-in-part of U.S. patent application Ser. No. 13/559,917, filed Jul. 27, 2012, which is a continuation-in-part of Ser. No. 13/267,119, filed Oct. 6, 2011, which claims priority to U.S. Provisional Application 61/535,726, filed on Sep. 16, 2011, the entire contents of which are incorporated by reference.

FIELD OF THE INVENTION

The present application is generally directed to orthopedic systems, and in particular, to systems including plates and spacers.

BACKGROUND

Spinal discs and/or vertebral bodies of a spine can be displaced or damaged due to trauma, disease, degenerative defects, or wear over an extended period of time. One result of this displacement or damage may be chronic back pain. In some cases, to alleviate back pain, the disc can be removed and replaced with an implant, such as a spacer, that promotes fusion. In addition to providing one or more spacers, a plating system can be used to further stabilize the spine during the fusion process. Such a plating system can include one or more plates and screws for aligning and holding vertebrae in a fixed position with respect to one another.

Accordingly, there is a need for improved systems involving plating systems and spacers for spinal fusion and stabilization.

SUMMARY OF THE INVENTION

Various systems, devices and methods related to plating systems are provided. In some embodiments, a spinal system comprises a spacer for inserting into an intervertebral space and a plate configured to abut the spacer. The spacer can include an upper surface, a lower surface and an opening that extends between the upper surface to the lower surface, wherein the spacer further includes a tapered leading end. The plate for abutting the spacer can include a plate body, a first opening formed in the plate body for receiving a first bone screw, a second opening formed in the plate body for receiving a second bone screw, a set screw, and a pair of extensions that extend from the plate body that are configured to engage the spacer. The first opening can angled in an upward direction, while the second opening can be angled in a downward direction. The set screw can be configured to prevent back-out of both the first and the second bone screws, wherein the set screw has a first position whereby the first and second bone screws can be inserted past the set screw and into the first and second openings and a second position following rotation of the set screw whereby the first and second bone screws are prevented from backing out by the set screw. A first bone screw is provided for inserting into the first opening in the plate body, wherein the first bone screw is configured to be inserted into a first vertebral body. A second bone screw is provided for inserting into the second opening in the plate body, wherein the second bone screw is configured to be inserted into a second vertebral body different from the vertebral body.

In other embodiments, a spinal system comprises a spacer for inserting into an intervertebral space and a plate configured to abut the spacer. The spacer can include an upper surface, a lower surface and an opening that extends between the upper surface to the lower surface, wherein the spacer further includes a concave leading end. The plate for abutting the spacer can include a plate body, a first opening formed in the plate body for receiving a first bone screw, a second opening formed in the plate body for receiving a second bone screw, a set screw, and a pair of extensions that extend from the plate body that are configured to engage the spacer. The first opening can angled in an upward direction, while the second opening can be angled in a downward direction. The set screw can be configured to prevent back-out of at least one of the first and the second bone screws, wherein the set screw has a first position whereby at least one of the first and second bone screws can be inserted past the set screw and into at least one of the first and second openings and a second position following rotation of the set screw whereby at least one of the first and second bone screws are prevented from backing out by the set screw. Each of the pair of extensions can include a window that extends along a length of the extension. A first bone screw is provided for inserting into the first opening in the plate body, wherein the first bone screw is configured to be inserted into a first vertebral body. A second bone screw is provided for inserting into the second opening in the plate body, wherein the second bone screw is configured to be inserted into a second vertebral body different from the vertebral body.

In some embodiments, a spinal system comprises a spacer for inserting into an intervertebral space and a plate configured to abut the spacer. The spacer can include an upper surface, a lower surface and an opening that extends between the upper surface to the lower surface. The plate for abutting the spacer can include a plate body, a first opening formed in the plate body for receiving a first bone screw, a second opening formed in the plate body for receiving a second bone screw, a set screw, and a pair of extensions that extend from the plate body that are configured to engage the spacer. The first opening can angled in an upward direction, while the second opening can be angled in a downward direction. The set screw can be configured to prevent back-out of at least one of the first and the second bone screws, wherein the set screw has a first position whereby at least one of the first and second bone screws can be inserted past the set screw and into at least one of the first and second openings and a second position following rotation of the set screw whereby at least one of the first and second bone screws are prevented from backing out by the set screw. Each of the pair of extensions can include a window that extends along a length of the extension. A first bone screw is provided for inserting into the first opening in the plate body, wherein the first bone screw is configured to be inserted into a first vertebral body. A second bone screw is provided for inserting into the second opening in the plate body, wherein the second bone screw is configured to be inserted into a second vertebral body different from the vertebral body. The spacer and the plate are independent from one another such that the spacer can be inserted into a desired spinal location prior to abutting the spacer with the plate.

DETAILED DESCRIPTION OF THE ILLUSTRATED EMBODIMENTS

The present application is generally directed to orthopedic systems, and in particular, to systems including plates and spacers.

The present application discloses orthopedic plating systems that can be used in spinal surgeries, such as spinal fusions. The plating systems disclosed herein include a plate and a spacer that are independent from one another. In some cases, the plate and the spacer can be pre-attached to one another before positioning them in a desired location of the spine. In other cases, the spacer can first be inserted into a desired location of the spine, and then the plate can be inserted thereafter. Advantageously, the plating systems disclosed herein are of low-profile. For example, they can provide a very small, anterior footprint cervical plate solution for fusion procedures. One skilled in the art will appreciate that while the plating systems can be used with cervical procedures, the plating systems are not limited to such areas, and can be used with other regions of the spine.

FIGS. 1A-1D illustrate different views of a plating system comprising a low profile plate attached to a spacer according to some embodiments. The plating system 5 includes a spacer 10 attached to a low-profile plate 50. Advantageously, the plating system 5 can be inserted through an anterior approach into a spine, and can desirably provide a small anterior footprint.

Figure 1A:
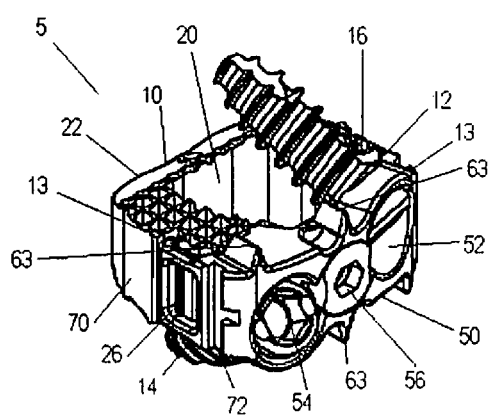
FIGS. 1A-1D illustrate different views of a low profile plate attached to a spacer according to some embodiments.
Figure 1B:
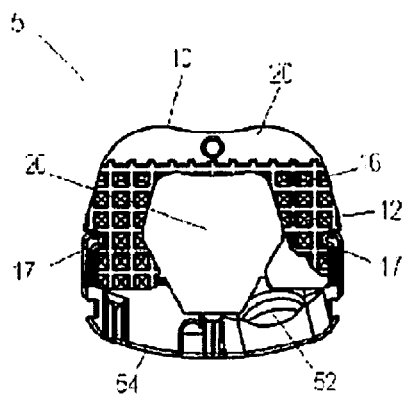

The spacer 10 is configured to have an upper surface 12, a lower surface 14, and a leading end 22. In some embodiments, the upper surface 12 and/or lower surface 14 includes texturing 16, such as teeth, ribs, ripples, etc. to assist in providing frictional contact with adjacent vertebral bodies. In some embodiments, the leading end 22 of the spacer 10 can be slightly tapered, as shown in FIG. 1A. With the taper, the leading end 22 can serve as a distraction surface that helps the spacer to be inserted into an intervertebral space. As shown in FIG. 1B, the leading end 22 can be concave, though in other embodiments, the leading end 22 can be straight or convex.

Figure 3A:
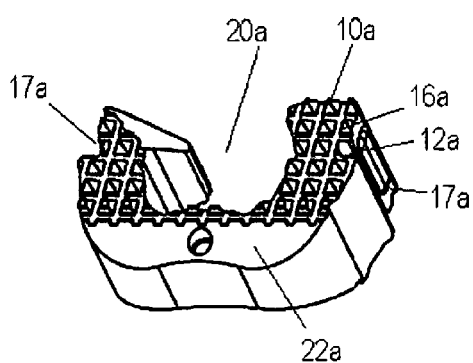
FIGS. 3A-3D illustrate different views of a PEEK spacer to be used with the low profile plate shown in FIGS. 2A-2D.
Figure 3B:
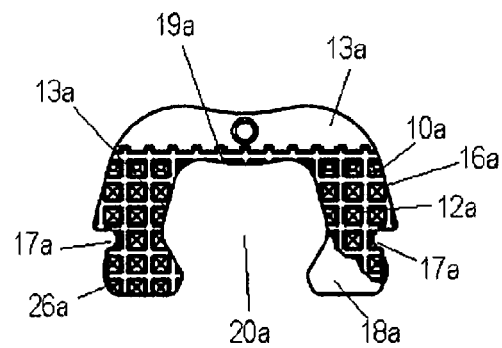

The spacer 10 can be substantially C-shaped (as shown in FIG. 3B), whereby it includes two side arms 13 that surround an inner opening 20. Adjacent the side arms 13 is a convex wall 19. In some embodiments, the convex wall 19 is substantially parallel to the concave surface of the leading end 22. The opening 20, which is configured to receive natural or synthetic graft material therein to assist in a fusion procedure, has an open side that is opposite convex wall 19, thereby giving the spacer 10 its C-shape.

The spacer 10 has a number of unique features that accommodate the attachment of a plate 50 thereto. Each of the side arms 13 of the spacer 10 includes a notch 17 (shown in FIG. 3B) for receiving a corresponding protrusion 71 of a lateral arm or extension 70 of the plate 50, thereby advantageously forming a first locking mechanism between the spacer 10 and the plate 50. In addition, in some embodiments, each of the side arms 13 of the spacer 10 can also include a hump region 26 (shown in FIG. 3B) that can extend in part into a window 72 of an attached plate 50 (shown in FIG. 2A), thereby advantageously providing a second locking mechanism between the spacer 10 and the plate 50. Advantageously, by providing secure first and second locking mechanisms between the spacer 10 and the plate 50, the plate and spacer will be kept securely together during any type of impaction of the plating system within the body. Furthermore, each of the side arms 13 of the spacer 10 can include a cut-away portion or chamfer 18, 19 (shown in FIG. 3C) to advantageously accommodate screws which pass through the plate. In embodiments that involve a pair of screws through the plate 50—one of which passes in an upward direction, and the other of which passes in a downward direction—one side arm 13 of the spacer 10 will include an upper chamfer 18 formed on an upper surface to accommodate the upwardly directed screw, while the second side arm 13 of the spacer will include a lower chamfer 19 formed on a lower surface to accommodate the downwardly directed screw.

Figure 4A:
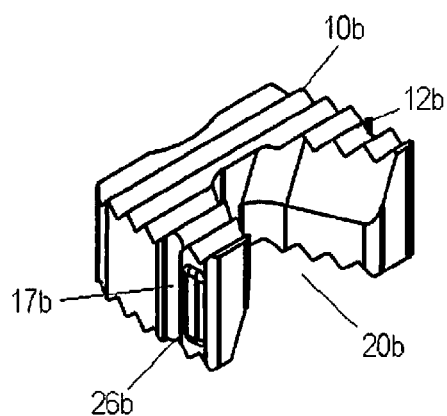
FIGS. 4A-4D illustrate different views of an allograft spacer to be used with the low profile plate shown in FIGS. 2A-2D.

The spacer 10 can be formed of any material. In some embodiments, the spacer 10 is formed of a polymer, such as PEEK, as shown in FIG. 3A. In some embodiments, the spacer 10 is formed of allograft bone, as shown in FIG. 4A. In some instances, to form an allograft implant, allograft bone may be cut or shaved from a desired bone member. The cut allograft bone will then be assembled together, using an adhesive or mechanical fastener (e.g., bone pins). Accordingly, in some embodiments, an allograft spacer 10 is formed of two, three, four or more layers that are assembled together, such as by one or more bone pins. One particular advantage of the invention is that the plate 50 can work with a variety of different spacers 10, as the plate 50 is independently removable from and attachable to the spacer 10. Regardless of whether a surgeon chooses to implant an allograft spacer or PEEK spacer 10 into an intervertebral space, the surgeon can simply attach the low-profile plate 50 to the spacer 10 following implantation into the intervertebral space.

The plate 50 is configured to have a plate body and a pair of lateral extensions 70 that extend from the plate body, each of which has a protrusion 71, for inserting into a corresponding notch 17 of the spacer 10. These lateral extensions 70 help form the first locking mechanism between the plate 50 and the spacer 10, as discussed above. In addition, the lateral extensions 70 of the plate 50 each include a window 72 (shown in FIG. 2A) for receiving a hump region 26 on the arms 17 of the spacer 10, thereby helping to form the second locking mechanism between the plate 50 and the spacer 10, as discussed above.

In addition to attaching to the spacer 10, the plate 50 is also configured to attach into one or more vertebral bodies via one or more bone screws. As shown in FIG. 1A, the plate 50 includes a first screw hole 52 and a second screw hole 54 for receiving bone screws therein. In some embodiments, screw hole 52 is angled upwardly such that an inserted bone screw passes upward into an upper vertebral body, while screw hole 54 is angled downwardly such that an inserted bone screw passes downward into a lower vertebral body. While the illustrated embodiment illustrates a pair of screw holes for receiving a pair of bone screws, it is possible to have one, three, four, five or more screw holes for receiving a different number of bone screws.

Figure 1C:
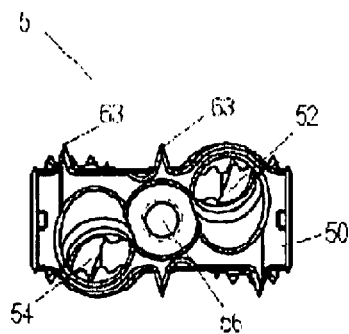
Figure 1D:
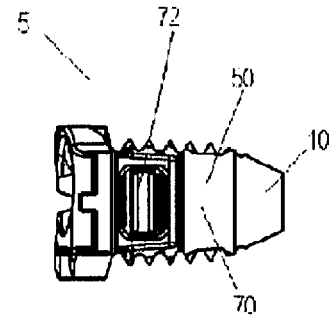

Over time, it is possible for bone screws to back-out. The plate 50 thus has a blocking or set screw 56 (shown in FIG. 1C) that assists in preventing back-out of inserted bone screws. As shown in FIG. 1C, the set screw 56 can be in an initial position that allows first and second bone screws to pass through holes 52, 54. Once the bone screws have been inserted through the holes 52, 54, the set screw 56 can be rotated (e.g., 90 degrees), to thereby block the bone screws and prevent back out of the bone screws. In some embodiments, the set screw 56 abuts a side of the head of the bone screws to prevent back-out of the bone screws, while in other embodiments, the set screw 56 rests over a top of the head of the bone screws to prevent back-out of the bone screws. In some embodiments, the set screw 56 comes pre-fixed with the plate 50. As shown in FIG. 1C, a single set screw 56 can be used to conveniently block a pair of bone screws. In other embodiments, each bone screw can be assigned its own set screw, which can operate independently of one another, to prevent back-out of the bone screw.

The plate 50 can also include one or more knife-like edges 63 that provide additional torsional stabilization when the plate 50 rests against a bone member. As shown in FIG. 1C, the knife-like edges 63 can be formed on both the upper and lower surfaces of the plate 50 body. While the illustrated embodiment shows a pair of knife-like edges 63 on an upper surface of the plate body and a pair of knife-like edges 63 on a lower surface of the plate body, one skilled in the art will appreciate that a different number of knife-like edges 63 can be provided.

FIGS. 2A-2D illustrate different views of the low profile plate shown in FIGS. 1A-1D. From these views, one can see the pair of lateral extensions 70 that extend from the body of the plate 50. At the distal end of each of the lateral extensions 70 is an inwardly-facing protrusion 71 that is configured to fit into a corresponding notch in the spacer 10. In addition, from these views, one can see the windows 72 that are formed in each of the lateral extensions 70. The windows 72 advantageously receive hump regions 26 of the spacer to provide a locking mechanism, and also help to improve desirable radiolucency. Advantageously, the windows 72 can have rounded edges to accommodate the spacer 10 therein. While the illustrated windows 72 are shown as rectangular with rounded edges, in other embodiments, the windows 72 can have a different shape, such as circular or oval. In some embodiments, the plate 50 is assembled axially to the spacer 10.

Figure 2A:
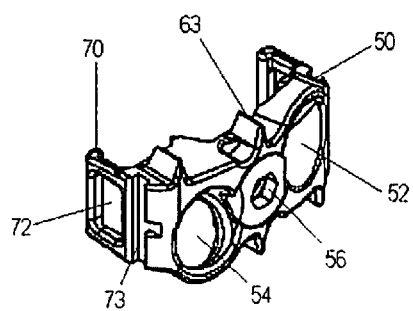
FIGS. 2A-2D illustrate different views of the low profile plate shown in FIGS. 1A-1D.
Figure 2B:
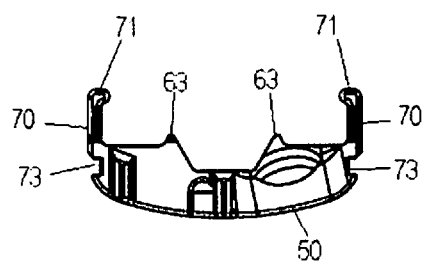
Figure 2C:
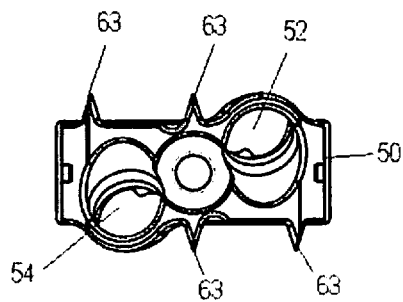
Figure 2D:
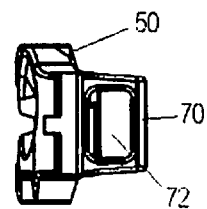
Figure 3C:
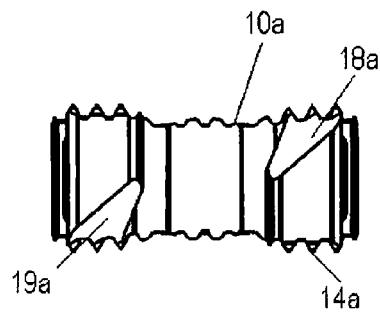
Figure 3D:
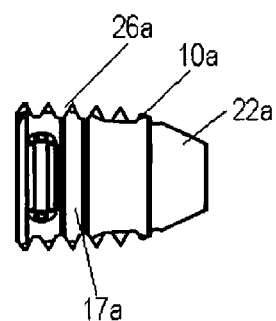

In some embodiments, the low profile plate 50 can also include indented gripping sections 73 (shown in FIGS. 2A and 2B). These indented gripping sections 73 advantageously provide a gripping surface for an insertion instrument, thereby facilitating easy delivery of the plate to a spacer body during surgery.

FIGS. 3A-3D illustrate different views of a PEEK spacer to be used with the low profile plate shown in FIGS. 2A-2D. From these views, one can see how the spacer 10a includes an upper surface 12a and a lower surface 14a with texturing 16a; a generally C-shaped body including a pair of arms 13a each having a notch 17a formed therein and an upper chamfer 18a or lower chamfer 19a; and a tapered leading edge 22a. In addition, one skilled in the art can appreciate the substantially symmetric shape of the inner opening 20a, which serves as a graft hole for receiving graft material therein.

Figure 4B:
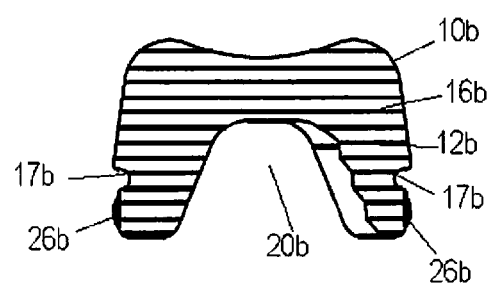
Figure 4C:
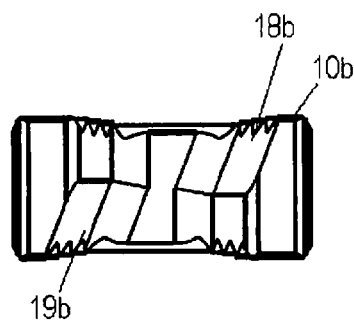
Figure 4D:
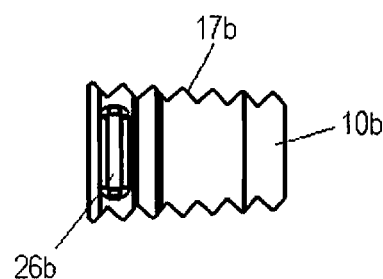

FIGS. 4A-4D illustrate different views of an allograft spacer to be used with the lower profile plate shown in FIGS. 2A-2D. While the allograft spacer 10b shares similar features to the PEEK spacer 10a shown in previous figures, such as the notches 17b, hump surfaces 26b, and chamfers 18b,19b, the allograft spacer 10b need not be the same. For example, the shape of the graft opening 20b can be more of an arch, as shown in FIG. 4B.

FIGS. 5A-5D illustrate different views of a second alternative embodiment of a low profile plate attached to a spacer according to some embodiments. Rather than having a plate 50 with lateral extensions 70 that extend around the outer surface of a spacer 10, the present embodiment of the plating system 105 includes a plate 150 with an enclosed posterior extension 155 that fits within the body of the spacer 110. The enclosed posterior extension 155 includes extending surfaces 166, 167 that are fitted into corresponding inlets 121, 123 formed in the body of the spacer 120, thereby forming a first locking mechanism between the plate 150 and the spacer 110. In addition, the enclosed posterior extension 155 of the plate 50 includes one or more deformable locking tabs 160 (shown in FIG. 6B) that securely lock into tab holes 181a in the spacer body 110, thereby forming a second locking mechanism between the plate 150 and the spacer 110. While in some embodiments, the plate 150 can be attached to the spacer 110 after inserting the spacer 110 into a desired location in the body, in other embodiments, the plate 150 can be pre-assembled with the spacer 110 prior to inserting the plating system 105 into the desired location.

Figure 7A:
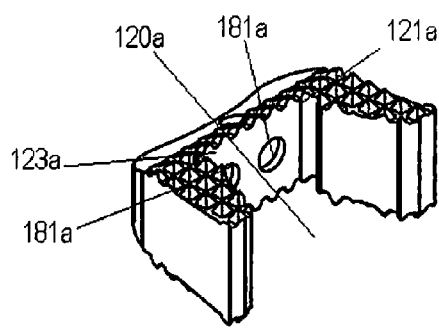
FIGS. 7A-7D illustrate different views of a PEEK spacer to be used with the low profile plate in FIGS. 6A-6D.

Like the spacer 10 in FIG. 1A, the spacer 110 is configured to have an upper surface 112, a lower surface 114, and a leading end 122. In some embodiments, the upper surface 112 and/or lower surface 114 includes texturing 116, such as teeth, ribs, ripples, etc. to assist in providing frictional contact with adjacent vertebral bodies. In some embodiments, the leading end 122 of the spacer 110 can be slightly tapered, as shown in FIG. 7D. With the taper, the leading end 122 can serve as a distraction surface that helps the spacer 110 to be inserted into an intervertebral space. As shown in FIG. 1B, the leading end 122 can be concave, though in other embodiments, the leading end 122 can be straight or convex.

Figure 7B:
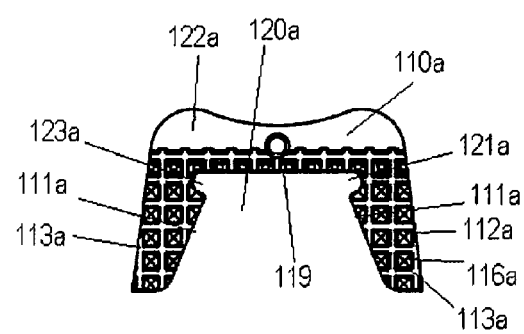
Figure 7C:
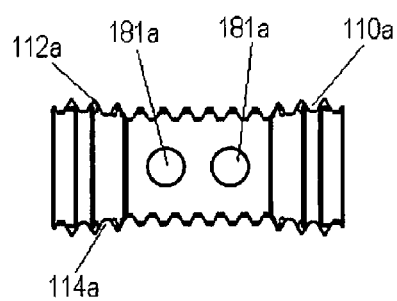
Figure 7D:
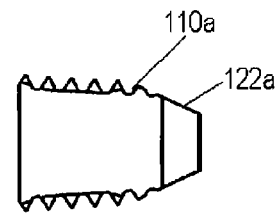

The spacer 110 can be substantially C-shaped (as shown in FIG. 7B), whereby it includes two side arms 113 that surround an inner opening 120. Adjacent the side arms 113 is a straight wall 119 that forms the border of the graft opening 120. The straight wall 119 can include one or more tab holes 181 (shown in FIG. 7A) for receiving deformable tab locks 160 therein. The graft opening 20, which is configured to receive natural or synthetic graft material therein to assist in a fusion procedure, has an open side that is opposite the straight wall 119, thereby giving the spacer 110 its C-shape.

In some embodiments, the graft opening 120 (shown in FIG. 7B) has a different shape from the opening 20 of the spacer 10 of the prior embodiment, as the graft opening 120 is configured to not only receive graft material, but also the enclosed posterior extension 155 of the plate 150. For example, the graft opening 120 includes two inlets—a first inlet 121 formed at the junction between the first arm 113 and wall 119 and a second inlet 123 formed at the junction between the second arm 113 and wall 119 (shown in FIG. 7B)—for receiving outwardly extending surfaces 166, 167 of the plate 150 (shown in FIG. 6B). In addition, the graft opening 120 includes two outwardly tapering walls 111 that provide enough space to accommodate any bone screws inserted in the plate 150. As such, additional chamfers 18, 19 (as shown in FIG. 3B) are optional.

Figure 8A:
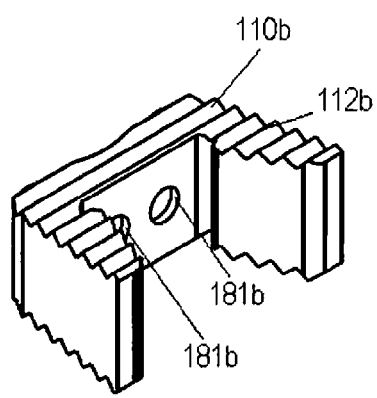
FIGS. 8A-8D illustrate different views of an allograft spacer to be used with the low profile plate in FIGS. 6A-6D.
Figure 8B:
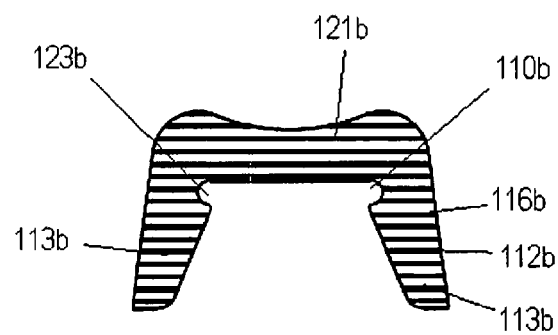
Figure 8C:
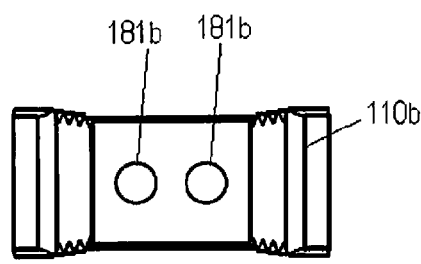
Figure 8D:
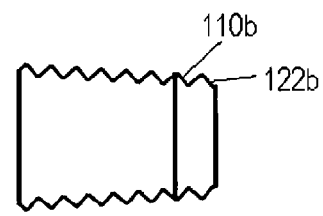

Like spacer 10, the spacer 110 can be formed of a variety of materials. In some embodiments, the spacer 110 comprises PEEK, as shown in FIG. 7A, while in other embodiments, the spacer 110 comprises allograft bone, as shown in FIG. 8A.

The plate 150 is configured to have a plate body, and an enclosed posterior extension 155 that extends from the plate body, which is received within and retains the spacer 110. The enclosed posterior extension 155 includes first and second outwardly extending surfaces 166, 167 that fit into inlets 121, 123 formed within the spacer 110 body to form a first locking mechanism. In addition, one or more deformable tab locks 160 extend from an exterior surface of the enclosed posterior extension 155 and are received in corresponding tab holes 181 in the spacer 150 to form a second locking mechanism. In some embodiments, the side walls of the enclosed posterior extension 155 can include one or more windows 172 (shown in FIG. 6A) for improving radiolucency of the plating system. In some embodiments, the plate 150 is assembled axially to the spacer 110.

Figure 5A:
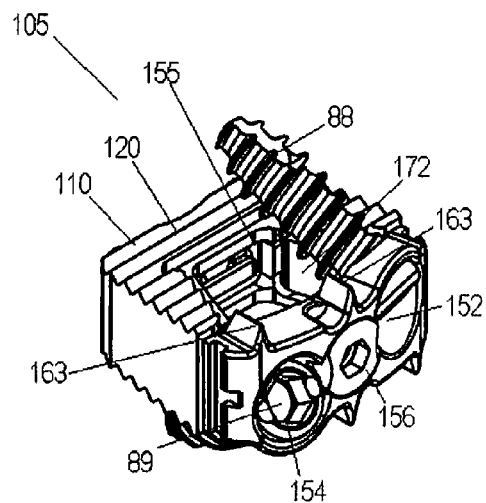
FIGS. 5A-5D illustrate different views of a second alternative embodiment of a low profile plate attached to a spacer according to some embodiments.
Figure 5B:
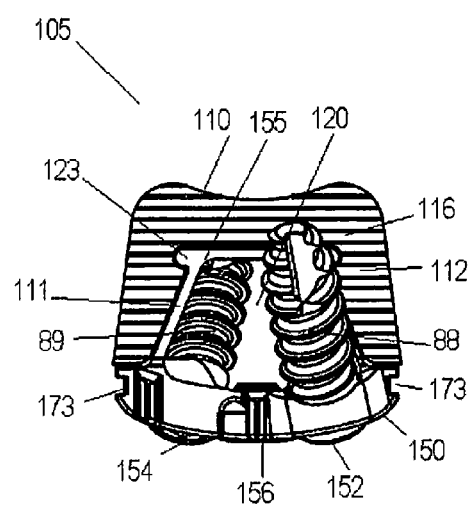

In addition to attaching to the spacer 110, the plate 150 is also configured to attach into one or more vertebral bodies via one or more bone screws 88, 89. As shown in FIG. 5A, the plate 150 includes a first screw hole 152 and a second screw hole 154 for receiving bone screws 88, 89 therein. In some embodiments, screw hole 152 is angled upwardly such that an inserted bone screw 88 passes upward into an upper vertebral body, while screw hole 154 is angled downwardly such that an inserted bone screw 89 passes downward into a lower vertebral body. While the illustrated embodiment illustrates a pair of screw holes for receiving a pair of bone screws, it is possible to have one, three, four, five or more screw holes for receiving a different number of bone screws.

Figure 5C:
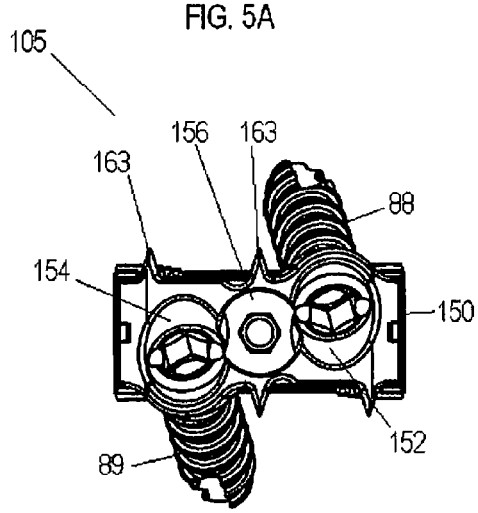
Figure 5D:
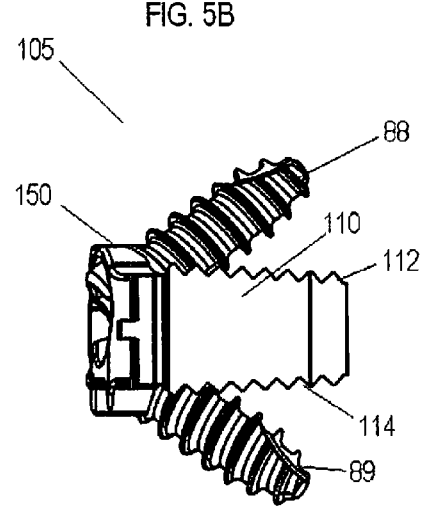

Over time, it is possible for bone screws to back-out. The plate 150 thus has a blocking or set screw 156 (shown in FIG. 5C) that assists in preventing back-out of inserted bone screws. As shown in FIG. 5C, the set screw 156 can be in an initial position that allows first and second bone screws to pass through holes 152, 154. Once the bone screws have been inserted through the holes 152, 154, the set screw 156 can be rotated (e.g., 90 degrees), to thereby block the bone screws and prevent back out of the bone screws. In some embodiments, the set screw 156 abuts a side of the head of the bone screws to prevent back-out of the bone screws, while in other embodiments, the set screw 156 rests over a top of the head of the bone screws to prevent back-out of the bone screws. In some embodiments, the set screw 156 comes pre-fixed with the plate 150. As shown in FIG. 5C, a single set screw 156 can be used to conveniently block a pair of bone screws. In other embodiments, each bone screw can be assigned its own set screw, which can operate independently of one another, to prevent back-out of the bone screw.

The plate 150 can also include one or more knife-like edges 163 that provide additional torsional stabilization when the plate 150 rests against a bone member. As shown in FIG. 5C, the knife-like edges 163 can be formed on both the upper and lower surfaces of the plate 150 body. While the illustrated embodiment shows a pair of knife-like edges 163 on an upper surface of the plate body and a pair of knife-like edges 163 on a lower surface of the plate body, one skilled in the art will appreciate that a different number of knife-like edges 163 can be provided.

FIGS. 6A-6D illustrate different views of the low profile plate shown in FIGS. 5A-5D. From these views, one can see the enclosed posterior extension 155 that extends from the body of the plate 150. At the distal end of the enclosed posterior extension 155 are a pair of outwardly extending surfaces 166, 167 that are configured to fit within inlets 121, 123 formed in the spacer. From these views, one can also see the deformable tab lock 160 (FIG. 6B) that can help secure the plate 150 to the spacer 110. In addition, from these views, one can see the windows 172 that are formed in each of the arms of the enclosed posterior extension 155. The windows 172 advantageously help to improve desirable radiolucency, and are of large size to provide a large viewing surface area. While the illustrated windows 172 are shown as triangular with rounded edges, in other embodiments, the windows 172 can have a different shape, such as circular or oval. In some embodiments, the plate 150 is assembled axially to the spacer 110.

Figure 6A:
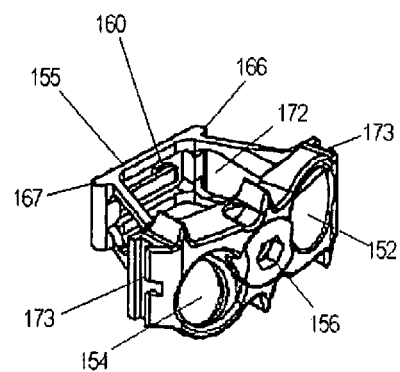
FIGS. 6A-6D illustrate different views of the low profile plate shown in FIGS. 5A-5D.
Figure 6B:
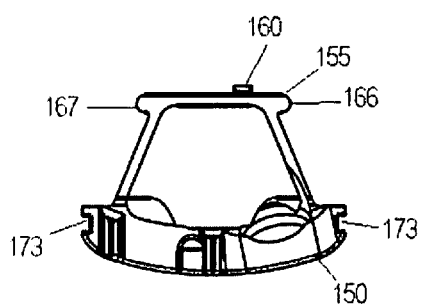
Figure 6C:
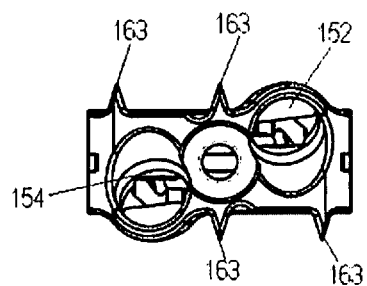
Figure 6D:
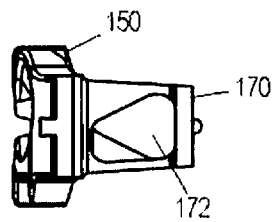

In some embodiments, the low profile plate 150 can also include indented gripping sections 173 (shown in FIGS. 6A and 6B). These indented gripping sections 173 advantageously provide a gripping surface for an insertion instrument, thereby facilitating easy delivery of the plate to a spacer body during surgery.

FIGS. 7A-7D illustrate different views of a PEEK spacer to be used with the low profile plate shown in FIGS. 5A-5D. From these views, one can see how the spacer 110a includes an upper surface 112a and a lower surface 114a with texturing 116a; a generally C-shaped body including a pair of arms 113a each having an inner inlet 121, 123a formed therein; and a tapered leading edge 122a. In addition, one skilled in the art can appreciate the substantially symmetric shape of the inner opening 120a, which serves as a graft hole for receiving graft material therein.

FIGS. 8A-8D illustrate different views of an allograft spacer to be used with the lower profile plate shown in FIGS. 5A-5D. While the allograft spacer 110b shares similar features to the PEEK spacer 110a shown in previous figures, such as the C-shaped body including a pair of arms 113b each having an inlet 121b, 123b formed therein, the allograft spacer 110b need not be the same.

FIGS. 9A-9D illustrate different views of a third alternative embodiment of a low profile plate attached to a spacer according to some embodiments. In the present embodiment, the plating system 205 includes a plate 250 having lateral arms or extensions 270 that extend around an exterior surface of a spacer 210. The lateral extensions 270 extend wider than the lateral extensions 70 in the first embodiment, and do not necessarily have to interlock with the spacer 210. While in some embodiments, the plate 250 can be attached to the spacer 210 after inserting the spacer 210 into a desired location in the body, in other embodiments, the plate 250 can be pre-assembled with the spacer 210 prior to inserting the plating system 205 into the desired location.

Figure 9A:
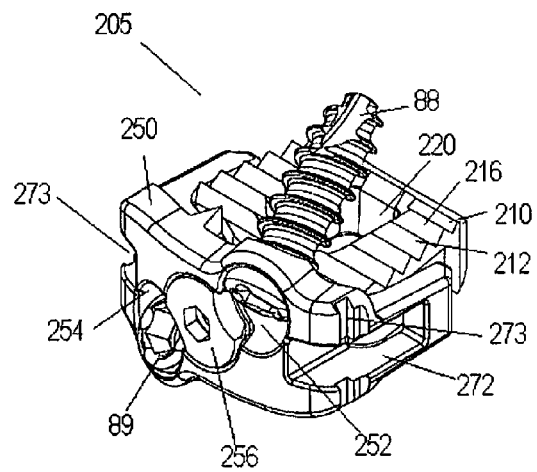
FIGS. 9A-9D illustrate different views of a third alternative embodiment of a low profile plate attached to a spacer according to some embodiments.
Figure 9B:
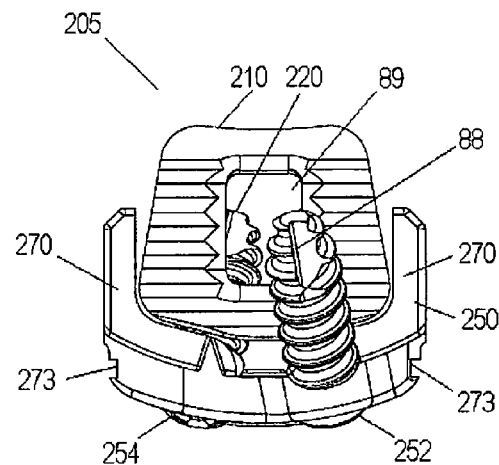
Figure 9C:
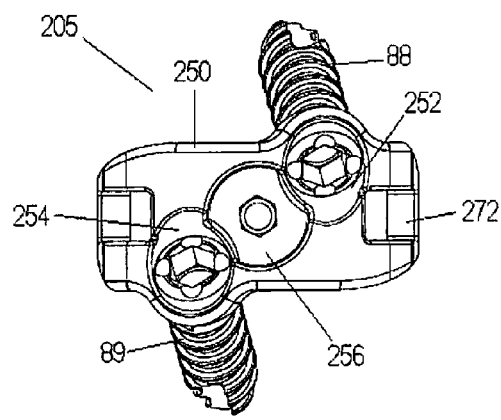
Figure 9D:
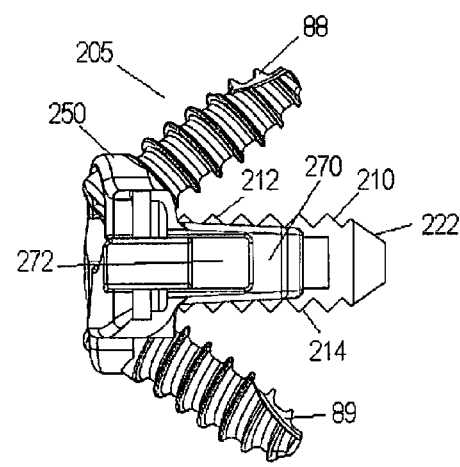

Like the spacer 10 in FIG. 1A, the spacer 210 is configured to have an upper surface 212, a lower surface 214, and a leading end 222. In some embodiments, the upper surface 212 and/or lower surface 214 includes texturing 216, such as teeth, ribs, ripples, etc. to assist in providing frictional contact with adjacent vertebral bodies. In some embodiments, the leading end 222 of the spacer 210 can be slightly tapered, as shown in FIG. 9D. With the taper, the leading end 222 can serve as a distraction surface that helps the spacer 210 to be inserted into an intervertebral space. As shown in FIG. 9B, the leading end 222 can be slightly concave, though in other embodiments, the leading end 122 can be straight or convex. Unlike previously illustrated spacers, the spacer 210 can have a graft hole 220 that is completely enclosed. As shown in FIG. 9B, the graft hole 220 can surrounded by four walls. In addition, the spacer 210 can include four outer walls: two straight walls, a convex wall and a concave wall.

In some embodiments, the graft opening 220 (shown in FIG. 9B) has a different shape from the openings of prior embodiments, as the graft opening 220 is enclosed. While the graft opening 220 is rectangular with rounded edges, in other embodiments, the graft opening 220 can have a different shape. For example, in some embodiments, the graft opening 220 can have curved walls, instead of straight walls, or can have tapered walls, instead of straight walls.

Like spacer 10, the spacer 210 can be formed of a variety of materials. In some embodiments, the spacer 210 comprises allograft bone, while in other embodiments, the spacer 210 comprises PEEK.

The plate 250 is configured to have a pair of lateral extensions 270 that receive the spacer 220. As shown in FIG. 9A, in some embodiments, the lateral extensions 270 include one or more windows 272 for improving radiolucency of the plating system. In some embodiments, the plate 250 is assembled axially to the spacer 210.

In addition to capturing the spacer 210, the plate 250 is also configured to attach into one or more vertebral bodies via one or more bone screws 88, 89. As shown in FIG. 9A, the plate 250 includes a first screw hole 252 and a second screw hole 254 for receiving bone screws 88, 89 therein. In some embodiments, screw hole 252 is angled upwardly such that an inserted bone screw 88 passes upward into an upper vertebral body, while screw hole 254 is angled downwardly such that an inserted bone screw 89 passes downward into a lower vertebral body. While the illustrated embodiment illustrates a pair of screw holes for receiving a pair of bone screws, it is possible to have one, three, four, five or more screw holes for receiving a different number of bone screws.

Over time, it is possible for bone screws to back-out. The plate 250 thus has a blocking or set screw 256 (shown in FIG. 9C) that assists in preventing back-out of inserted bone screws. As shown in FIG. 9C, the set screw 256 can be in an initial position that allows first and second bone screws to pass through holes 252, 254. Once the bone screws have been inserted through the holes 252, 254, the set screw 256 can be rotated (e.g., 90 degrees), to thereby block the bone screws and prevent back out of the bone screws. In some embodiments, the set screw 256 abuts a side of the head of the bone screws to prevent back-out of the bone screws, while in other embodiments, the set screw 256 rests over a top of the head of the bone screws to prevent back-out of the bone screws. In some embodiments, the set screw 256 comes pre-fixed with the plate 250. As shown in FIG. 9C, a single set screw 256 can be used to conveniently block a pair of bone screws. In other embodiments, each bone screw can be assigned its own set screw, which can operate independently of one another, to prevent back-out of the bone screw.

FIGS. 10A-10D illustrate different views of the low profile plate shown in FIGS. 9A-9D. From these views, one can see the lateral extensions 270 that extend from the body of the plate 250. From these views, one can also see the windows 272 (FIG. 10A) that extend along a substantial length of the lateral extensions 270. In some embodiments, each window 272 has a length greater than half the length of each lateral extension 270, thereby advantageously increasing the radiolucency of the plating system. In some embodiments, the plate 250 is assembled axially to the spacer 210.

Figure 10A:
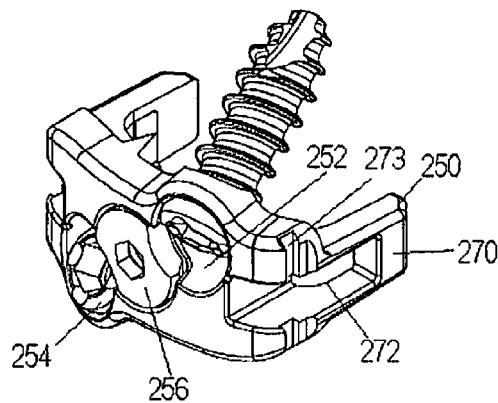
FIGS. 10A-10D illustrate different views of the low profile plate shown in FIGS. 9A-9D.
Figure 10B:
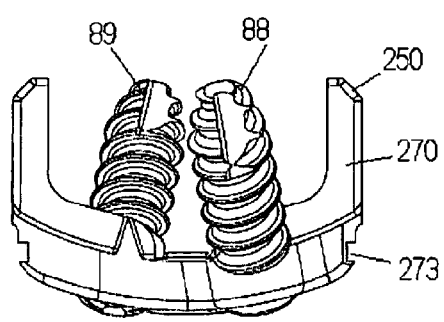
Figure 10C:
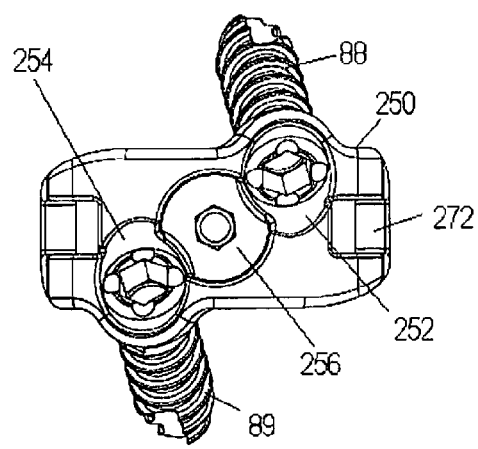
Figure 10D:
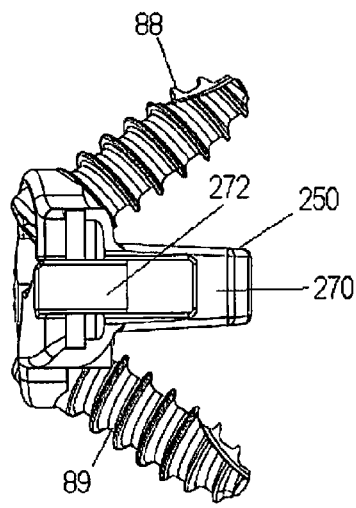

In some embodiments, the low profile plate 250 can also include indented gripping sections 273 (shown in FIGS. 10A and 10B). These indented gripping sections 273 advantageously provide a gripping surface for an insertion instrument, thereby facilitating easy delivery of the plate to a spacer body during surgery.

FIGS. 11A-11D illustrate different views of a fourth alternative embodiment of a low profile plate attached to a spacer according to some embodiments. Like the previous embodiment, the plating system 305 includes a plate 350 having lateral arms or extensions 370 that extend around an exterior surface of a spacer 310. The lateral extensions 370 extend wider than the lateral extensions 70 in the first embodiment, and do not necessarily have to interlock with the spacer 310. While in some embodiments, the plate 350 can be attached to the spacer 310 after inserting the spacer 310 into a desired location in the body, in other embodiments, the plate 350 can be pre-assembled with the spacer 310 prior to inserting the plating system 305 into the desired location.

Figure 11A:
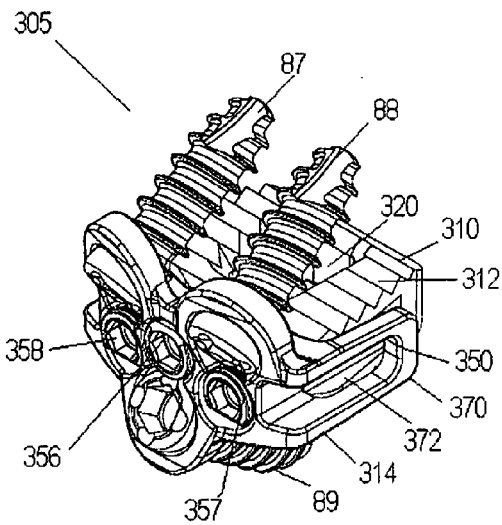
FIGS. 11A-11D illustrate different views of a fourth alternative embodiment of a low profile plate attached to a spacer according to some embodiments.
Figure 11B:
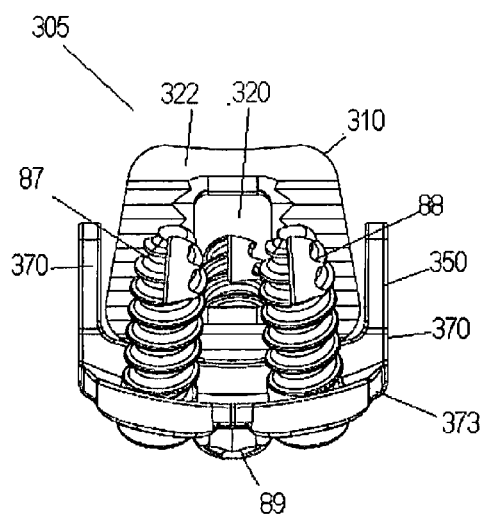
Figure 11C:
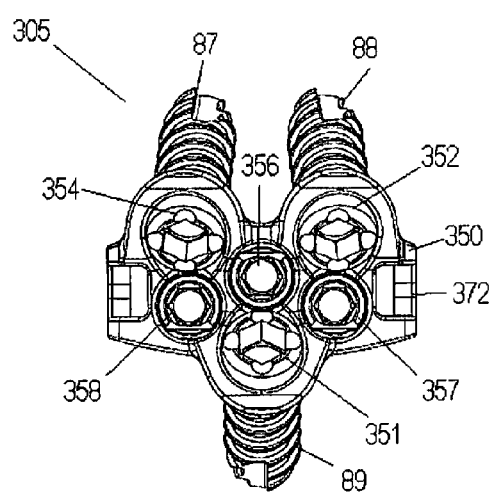
Figure 11D:
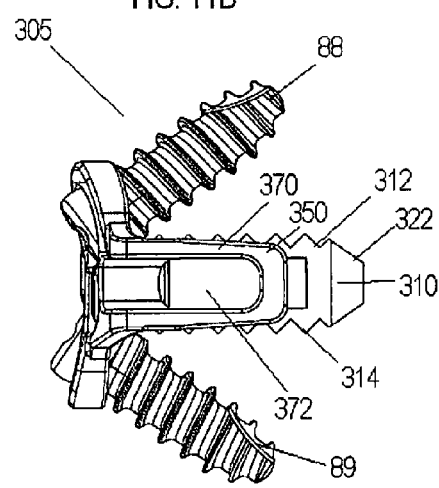

Like the spacer 10 in FIG. 1A, the spacer 310 is configured to have an upper surface 312, a lower surface 314, and a leading end 322. In some embodiments, the upper surface 312 and/or lower surface 314 includes texturing 316, such as teeth, ribs, ripples, etc. to assist in providing frictional contact with adjacent vertebral bodies. In some embodiments, the leading end 322 of the spacer 310 can be slightly tapered, as shown in FIG. 11D. With the taper, the leading end 322 can serve as a distraction surface that helps the spacer 310 to be inserted into an intervertebral space. As shown in FIG. 11B, the leading end 322 can be slightly concave, though in other embodiments, the leading end 322 can be straight or convex. In some embodiments, the spacer 310 can have a graft hole 320 that is completely enclosed. As shown in FIG. 11B, the graft hole 320 can surrounded by four walls. In addition, the spacer 320 can be comprised of four outer walls: two straight, one concave and one convex.

In some embodiments, the graft opening 320 (shown in FIG. 11B) of the spacer 310 is enclosed. While the graft opening 320 is rectangular with rounded edges, in other embodiments, the graft opening 320 can have a different shape. For example, in some embodiments, the graft opening 320 can have curved walls, instead of straight walls, or can have tapered walls, instead of straight walls.

Like spacer 10, the spacer 310 can be formed of a variety of materials. In some embodiments, the spacer 210 comprises allograft bone, while in other embodiments, the spacer 310 comprises PEEK.

The plate 350 is configured to have a pair of lateral extensions 370 that receive the spacer 320. As shown in FIG. 11A, in some embodiments, the lateral extensions 370 include one or more windows 372 for improving radiolucency of the plating system. In some embodiments, the plate 350 is assembled axially to the spacer 310.

In addition to capturing the spacer 310, the plate 350 is also configured to attach into one or more vertebral bodies via one or more bone screws 88, 89. As shown in FIG. 9A, the plate 350 includes a first screw hole 351, a second screw hole 352 and a third screw hole 354 for receiving bone screws 87, 88, 89 therein. In some embodiments, screw holes 352 and 354 are angled upwardly such that inserted bone screws 87, 88 pass upward into an upper vertebral body, while screw hole 351 is angled downwardly such that inserted bone screw 89 passes downward into a lower vertebral body. While the illustrated embodiment illustrates three screw holes for receiving three bone screws, it is possible to have one, two, four, five or more screw holes for receiving a different number of bone screws.

Figure 12A:
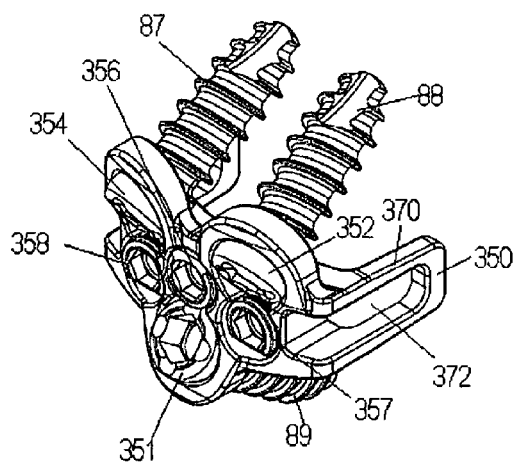
FIGS. 12A-12D illustrate different views of the low profile plate shown in FIGS. 11A-11D.
Figure 12B:
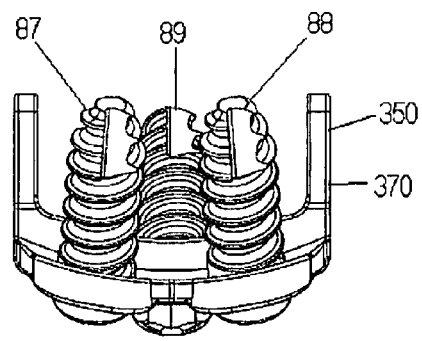
Figure 12C:
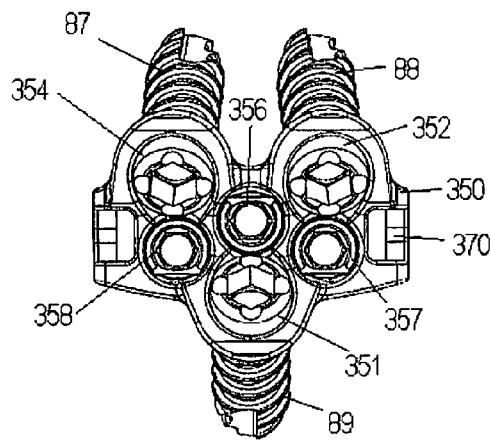
Figure 12D:
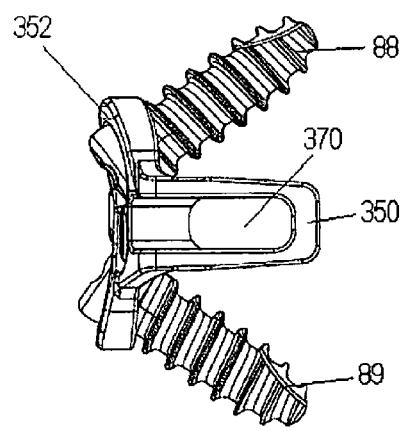

Over time, it is possible for bone screws to back-out. The plate 350 thus has blocking or set screws 356, 357, 358 (shown in FIG. 12C), each of which corresponds to one of screw holes 351, 352, 354. As shown in FIG. 12C, the set screws 356, 357, 358 can be in an initial position that allows first, second and third bone screws to pass through holes 351, 352, 354. Once the bone screws have been inserted through the holes 351, 352, 354, the set screws 356, 357, 358 can be rotated (e.g., 90 degrees), to thereby block the bone screws and prevent back out of the bone screws. In some embodiments, the set screws 356, 357, 358 abut a side of the head of the bone screws to prevent back-out of the bone screws, while in other embodiments, the set screws 356, 357, 358 rest over a top of the head of the bone screws to prevent back-out of the bone screws. In some embodiments, the set screws 356, 357, 358 come pre-fixed with the plate 350. As shown in FIG. 12C, a single set screw 356, 357, 358 can be used to conveniently block a single bone screws. In other embodiments, each set screw can be designed to block more than one set screw to prevent back-out of the bone screw.

FIGS. 12A-12D illustrate different views of the low profile plate shown in FIGS. 11A-11D. From these views, one can see the lateral extensions 370 that extend from the body of the plate 350. From these views, one can also see the windows 372 (FIG. 12A) that extend along a substantial length of the lateral extensions 370. In some embodiments, each window 372 has a length greater than half the length of each lateral extension 370, thereby advantageously increasing the radiolucency of the plating system. In some embodiments, the plate 350 is assembled axially to the spacer 310.

The plating systems describe include a plate that is independent from a spacer. The plate is low-profile and can be used with any type of spacer, such as allograft or PEEK.

FIGS. 13A-13D illustrate different views of a multi-piece allograft spacer to be used with the low profile plates discussed above according to some embodiments. The multi-piece allograft spacer 410 can be formed of an upper member 436 and a lower member 438 that are connected together via one or more pins 475. The upper member 436 and the lower member 438 each include cut-out portions that help form a graft opening 420 in the spacer 410.

The upper member 436 can include an upper surface having bone engagement surfaces (e.g., ridges, teeth, ribs) and a lower interfacing surface 446. The lower member 438 can include a lower surface having bone engagement surfaces (e.g., ridges, teeth, ribs) and an upper interfacing surface 448. In some embodiments, the upper member 436 can include one or more holes 462, while the lower member 438 can include one or more holes 464 which align with the one or more holes 462 of the upper member. The aligned holes are configured to receive one or more pins 475 to keep the upper and lower members of the allograft spacer together. In some embodiments, the pins 475 are also formed of bone material, such as allograft.

Figure 13A:
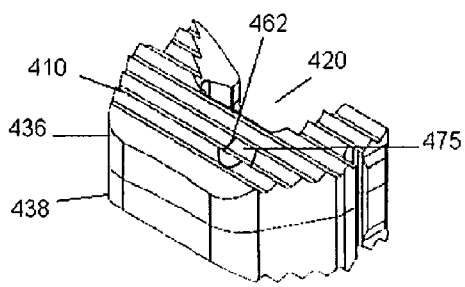
FIGS. 13A-13D illustrate different views of a multi-piece allograft spacer to be used with the low profile plates discussed above according to some embodiments.
Figure 13B:
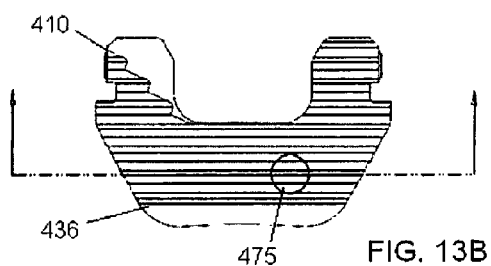
Figure 13C:
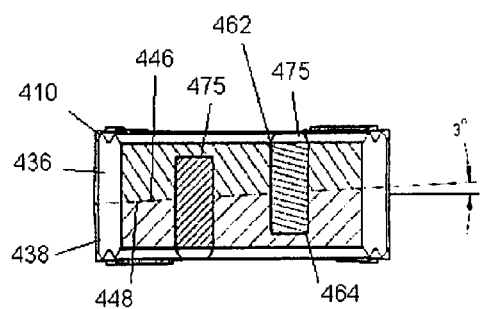
Figure 13D:
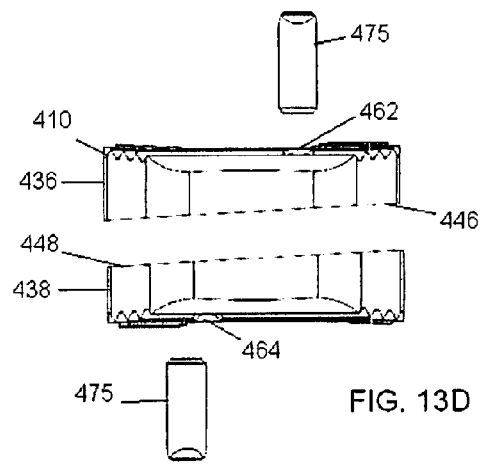

As shown best in FIG. 13C, the lower interfacing surface 446 of the upper member 436 is directly engaged with the upper interfacing surface 448 of the lower member 438. While the lower interfacing surface 446 and the upper interfacing surface 448 can be flat-on-flat, as both surfaces are planar, in some embodiments (as shown in FIG. 13C), the interface between the two surfaces is at an angle relative to the holes for receiving the pins 475. In other words, the pins 475 are received at an angle to the interface between the upper member 436 and the lower member 438. In addition, as shown in FIG. 13C, holes 462 and 464 need not go through the entirety of their respective members. For example, as shown in FIG. 13C, while hole 462 goes entirely through the upper and lower surface of the upper member 436, hole 464 goes only through the upper surface of the lower member 438, and does not go through to the lower surface. Accordingly, in some embodiments, aligned holes 462 and 464 create a "blind" pin-hole, whereby the hole does not go through the uppermost and lowermost surfaces of the spacer 410. Advantageously, in some embodiments, the use of such blind holes for receiving pins helps to maintain the pins within the spacer body.

FIGS. 14A-14D illustrate different views of an alternative multi-piece allograft spacer to be used with the lower profile plates discussed above according to some embodiments. The multi-piece allograft spacer 510 can be formed of a left member 536 and a right member 538 that are connected together in series or side-by-side (e.g., laterally) via one or more pins 575. The left member 536 and the right member 538 each include cut-out portions that help form a graft opening 520 in the spacer 510.

The left member 536 can include upper and lower surfaces having bone engagement surfaces (e.g., ridges, teeth, ribs). In addition, the left member 536 further includes a right interfacing surface 546. The right member 538 can also include upper and lower surfaces having bone engagement surfaces (e.g., ridges, teeth, ribs). In addition, the right member 538 further includes a left interfacing surface 548. In some embodiments, the left member 536 can include one or more holes 562, while the right member 538 can include one or more holes 564 which align with the one or more holes 562 of the left member. The aligned holes are configured to receive one or more pins 575 to keep the left and right members of the allograft spacer together.

Figure 14A:
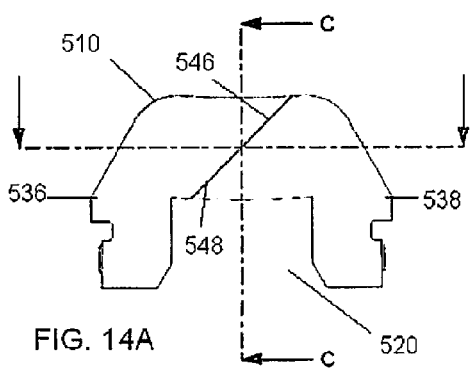
FIGS. 14A-14D illustrate different views of an alternative multi-piece allograft spacer to be used with the lower profile plates discussed above according to some embodiments.
Figure 14B:
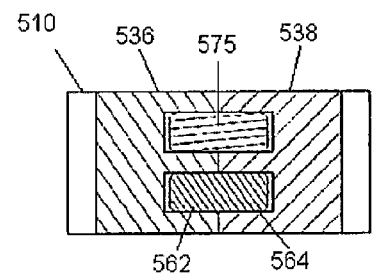
Figure 14C:
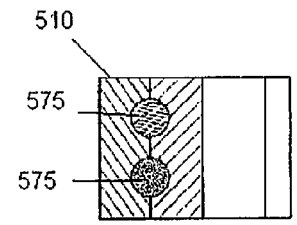
Figure 14D:
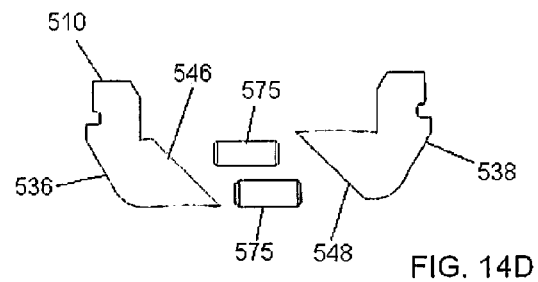

As shown best in FIG. 14A, the right interfacing surface 546 of the left member 536 is directly engaged with the left interfacing surface 548 of the right member 538. While the right interfacing surface 546 and the left interfacing surface 548 can be flat-on-flat, as both surfaces are planar, in some embodiments (as shown in FIG. 14A), the interface between the two surfaces is at an angle relative to the holes for receiving the pins 575. In other words, the pins 575 are received at an angle to the interface between the left member 536 and the right member 538. In addition, as shown in FIG. 14B, holes 562 and 564 need not go through the entirety of their respective members. In other words, one or more of the holes (e.g., holes 562, 564 or combined) can be blind holes, whereby the holes do not go through the left and right surfaces of the lateral implants.

By having multi-piece allograft spacers that are either stacked or aligned side-by-side, it is possible to have spacers of increased height and width. While the embodiments herein show two piece spacers, one skilled in the art will appreciate that three or more members can be combined to form multi-piece allograft spacers for use with any of the plate members described above.

It will be apparent to those skilled in the art that various modifications and variations can be made in the present invention without departing from the scope or spirit of the invention. Moreover, the improved bone screw assemblies and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone screw assemblies. Thus, it is intended that the present invention cover the modifications and variations of this invention provided that they come within the scope of the appended claims or their equivalents.

What is claimed is:

1. A spinal system comprising:
a spacer for inserting into an intervertebral space, the spacer including:
an upper surface,
a lower surface,
an opening that extends between the upper surface to the lower surface, wherein the spacer is formed of a first member operably coupled to a second member,
a first arm, and
a second arm, wherein an upper chamfer is formed on a distal most end of the first arm and a lower chamfer is formed on a distal most end of the second arm; and
a plate for abutting the spacer, the plate including:
a plate body,
a first opening formed in the plate body for receiving a first bone screw, wherein the first opening is angled in an upward direction;
a second opening formed in the plate body for receiving a second bone screw, wherein the second opening is angled in a downward direction;
a set screw for preventing back-out of both the first and the second bone screws, wherein the set screw has a first position whereby the first and second bone screws can be inserted past the set screw and into the first and second openings and a second position following rotation of the set screw whereby the first and second bone screws are prevented from backing out by the set screw, and
a pair of extensions that extend from the plate body, wherein the extensions are configured to extend around and engage outer sidewalls of the first and second arms, wherein a first extension of the pair of extensions includes a first enclosed window and a second extension of the pair of extensions includes a second enclosed window, wherein the first enclosed window receives a first notch that extends laterally outward from the outer sidewall of the first arm and the second enclosed window receives a second notch that extends laterally outward from the outer sidewall of the second arm.

2. The system of claim 1, wherein the spacer is a C-shaped spacer.

3. The system of claim 1, wherein the pair of extensions include inward protrusions for inserting into the outer sidewalls of the first and second arms.

4. The system of claim 3, wherein the notches correspond to the pair of extensions of the plate to form a first locking mechanism between the plate and the spacer.

5. The system of claim 1, wherein the opening in the spacer is bounded by at least one convex surface.

6. A spinal system comprising:
a spacer for inserting into an intervertebral space, the spacer including:
an upper surface,
a lower surface,
an opening that extends between the upper surface to the lower surface, wherein the spacer is formed of a first bone member attached to a second bone member,
a first arm, and
a second arm, wherein a first chamfer is formed in the first arm and a second chamfer is formed in the second arm;
a plate for abutting the spacer, the plate including:
a plate body,
a first opening formed in the plate body for receiving a first bone screw, wherein the first opening is angled in an upward direction;
a second opening formed in the plate body for receiving a second bone screw, wherein the second opening is angled in a downward direction;
a set screw for preventing back-out of at least one of the first and the second bone screws, wherein the set screw has a first position whereby at least one of the first and second bone screws can be inserted past the set screw and into at least one of the first and second openings and a second position following rotation of the set screw whereby at least one of the first and second bone screws is prevented from backing out by the set screw, and
a first extension and a second extension that extend from the plate body, wherein the first and second extensions are configured to extend around and engage outer sidewalls of the first and second arms, wherein the first extension includes a first enclosed window and the second extension includes a second enclosed window, wherein the first enclosed window receives a first notch that extends laterally outward from the outer sidewall of the first arm and the second enclosed window receives a second notch that extends laterally outward from the outer sidewall of the second arm;
a first bone screw for inserting into the first opening in the plate body, wherein the first bone screw is configured to be inserted into a first vertebral body; and
a second bone screw for inserting into the second opening in the plate body, wherein the second bone screw is configured to be inserted into a second vertebral body different from the vertebral body.

7. The system of claim 6, wherein the extensions of the plate comprise lateral extensions that engage the outer sidewalls of the first and second arms.

8. The system of claim 6, wherein the extensions of the plate comprise inward protrusions that extend into notches formed on the outer sidewalls of the first and second arms.

9. The system of claim 6, wherein the set screw is configured to prevent back-out of both the first and the second bone screws in the plate.

10. The system of claim 9, wherein upon rotation of the set screw, the set screw abuts side surfaces of heads of the first and second bone screws.

11. The system of claim 6, wherein the leading end of the spacer is tapered.

12. A spinal system comprising:
a spacer for inserting into an intervertebral space, wherein the spacer is formed of a first member attached to a second member by a pin, wherein the spacer further comprises a first arm and a second arm, wherein a first chamfer is formed on the first arm and a second chamfer is formed on the second arm;

a plate for abutting the spacer, the plate including:

a plate body, a first opening formed in the plate body for receiving a first bone screw, wherein the first opening is angled in an upward direction;

a second opening formed in the plate body for receiving a second bone screw, wherein the second opening is angled in a downward direction; and a first extension and a second extension that extend from the plate body, wherein the first and second extensions are configured to extend around and engage outer sidewalls of the first and second arms, wherein the first extension includes a first enclosed window and the second extension includes a second enclosed window, wherein the first enclosed window receives a first notch that extends laterally outward from the outer sidewall of the first arm and the second enclosed window receives a second notch that extends laterally outward from the outer sidewall of the second arm;

a first bone screw for inserting into the first opening in the plate body, wherein the first bone screw is configured to be inserted into a first vertebral body; and a second bone screw for inserting into the second opening in the plate body, wherein the second bone screw is configured to be inserted into a second vertebral body different from the vertebral body, wherein the spacer and the plate are independent from one another such that the spacer can be inserted into a desired spinal location prior to abutting the spacer with the plate.

13. The system of claim 12, wherein the spacer comprises an allograft spacer.

14. The system of claim of claim 13, wherein the allograft spacer is formed of an upper member and a lower member held together via a pin that extends through a hole in the allograft spacer, wherein the hole opens through an upper surface of the allograft spacer but does not extend through a lower surface of the allograft spacer.

15. The system of claim 12, wherein the spacer comprises a blind pin hole for receiving the pin.

16. The system of claim 12, wherein the enclosed windows of the first and second extensions receive the notches of the first and second arms to create a locking mechanism between the plate and the spacer.

* * * * *